US012807560B2

(12) United States Patent
Lee et al.

(10) Patent No.: US 12,807,560 B2
(45) Date of Patent: Nov. 24, 2026

(54) AMINOAROMATIC COMPOUND OR PHARMACEUTICALLY ACCEPTABLE SALT THEREOF, AND PHARMACEUTICAL COMPOSITION FOR PREVENTING OR TREATING NEURODEGENERATIVE DISEASES COMPRISING SAME AS ACTIVE INGREDIENT

(71) Applicants: INSTITUTE FOR BASIC SCIENCE, Daejeon (KR); KOREA INSTITUTE OF SCIENCE AND TECHNOLOGY, Seoul (KR)

(72) Inventors: Chang Jun Lee, Daejeon (KR); Heejung Chun, Seoul (KR); Woojin Won, Seoul (KR); Ki Duk Park, Seoul (KR); Jong Hyun Park, Seoul (KR); Ae Nim Pae, Seoul (KR); Ji Won Choi, Seoul (KR); Elijah Lee, Seoul (KR); Sun Jun Park, Seoul (KR); Hyeon Jeong Kim, Seoul (KR); Yoowon Kim, Seoul (KR); Byung Eun Kim, Seoul (KR); Siwon Kim, Seoul (KR)

(73) Assignees: INSTITUTE FOR BASIC SCIENCE, Daejeon (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 533 days.

(21) Appl. No.: 18/036,847

(22) PCT Filed: Nov. 12, 2021

(86) PCT No.: PCT/KR2021/016542

§ 371 (c)(1),
(2) Date: May 12, 2023

(87) PCT Pub. No.: WO2022/103201

PCT Pub. Date: May 19, 2022

(65) Prior Publication Data

US 2023/0406812 A1 Dec. 21, 2023

(30) Foreign Application Priority Data

Nov. 13, 2020 (KR) ........................ 10-2020-0152267
Nov. 11, 2021 (KR) ........................ 10-2021-0155076

(51) Int. Cl.

| | |
|---|---|
| ***C07C 211/53*** | (2006.01) |
| ***A23L 33/10*** | (2016.01) |
| ***A61P 25/28*** | (2006.01) |
| ***C07C 211/50*** | (2006.01) |
| ***C07C 217/60*** | (2006.01) |

(52) U.S. Cl.

CPC ............ *C07C 211/53* (2013.01); *A23L 33/10* (2016.08); *A61P 25/28* (2018.01); *C07C 211/50* (2013.01); *C07C 217/60* (2013.01)

(58) Field of Classification Search

None

See application file for complete search history.

(56) References Cited

U.S. PATENT DOCUMENTS

| | | | |
|---|---|---|---|
| 2004/0192693 A1 | 9/2004 | Schwink et al. |
| 2017/0001949 A1 | 1/2017 | Xie et al. |
| 2017/0037008 A1 | 2/2017 | Zhang et al. |

FOREIGN PATENT DOCUMENTS

| | | |
|---|---|---|
| DE | 10237932 A1 | 10/2003 |
| JP | 2000-239243 A | 9/2000 |
| KR | 10-2005-0115919 A | 12/2005 |
| KR | 10-2007-0001234 A | 1/2007 |
| KR | 10-2010-0050502 A | 5/2010 |
| WO | 2020/157126 A1 | 8/2020 |

OTHER PUBLICATIONS

Gastaldi et al. ((Jun. 29, 2021), Chemical Modulation of the 1-(Piperidin-4-yl)-1,3-dihydro-2H-benzo[d]imidazole-2-one Scaffold as a Novel NLRP3 Inhibitor, Molecules, 26, 1-35 (Year: 2021).*

Translation of specification for German Patent Application No. DE 10237932 A1 to Georg et. al. (herein after Georg'932; cited on the IDS dated Oct. 30, 2024, English translation used). (Year: 2003).*

Patani et al. (1996) Bioisosterism A rational approach in drug design, Chem. Rev., 96, 3147-3176 (Year: 1996).*

Kentaro Okano et al., "Synthesis of Secondary Arylamines through Copper-Mediated Intermolecular Aryl Amination", Organic Letters, vol. 5 No. 26, pp. 4987-4990, Oct. 4, 2003, cited in NPL No. 8.

H. Zellner et al., "Syntheses of quinoxaline derivatives", vol. 49, No. 106-107 , pp. 913-939, 1966, with its English Abstract, cited in NPL No. 8.

Ting Yang et al., "Discovery of Tertiary Amine and Indole Derivatives as Potent RORγt Inverse Agonists", ACS Medicinal Chemistry Letters, 4 pages, Nov. 22, 2013, cited in NPL No. 8.

Medchem News , vol. 15, No.3 , pp. 38-49 , Aug. 1, 2005, cited in NPL No. 8.

RN 1153534-47-4 Registry, Database Registry [Online], Retrieved from STN, Apr. 30, 2024, cited in NPL No. 8.

(Continued)

*Primary Examiner* — Kortney L. Klinkel
*Assistant Examiner* — Dawanna Shar-Day White
(74) *Attorney, Agent, or Firm* — Hauptman Ham, LLP

(57) ABSTRACT

The present invention provides a novel aminoaromatic compound or a pharmaceutically acceptable salt thereof, a pharmaceutical composition that is for preventing or treating neurodegenerative diseases and comprises same as an active ingredient, and a health functional food composition for preventing or ameliorating neurodegenerative diseases.

14 Claims, 8 Drawing Sheets

(56) References Cited

OTHER PUBLICATIONS

RN 1505016-07-8 Registry, Database Registry [Online], Retrieved from STN, Apr. 30, 2024, cited in NPL No. 8.
RN 1520989-82-5 Registry, Database Registry [Online], Retrieved from STN, Apr. 30, 2024, cited in NPL No. 8.
Japanese Office Action issued on Jun. 24, 2024, in connection with the Japanese Patent Application No. 2023-528546 with its English translation, 12 pages.
Korean Notice of Allowance dated Feb. 13, 2024 for corresponding Korean Patent Application No. 10-2021-0155076, along with English machine translation (7 pages).
Chemical Abstract Compound. STNext. RN 1505016-07-8 (Dec. 27, 2013), 2 pages; Cited in International Search Report and Written Opinion submitted on May 12, 2023.
Chemical Abstract Compound. STNext. RN 1503919-77-4 (Dec. 26, 2013), RN 1534558-95-6 (Jan. 31, 2014), RN 1523189-59-4 (Jan. 17, 2014), 4 pages; Cited in International Search Report and Written Opinion submitted on May 12, 2023.
International Search Report dated Feb. 25, 2023 for corresponding International Patent Application No. PCT/KR2021/016542, 7 pages.
Written Opinion dated Feb. 25, 2023 for corresponding International Patent Application No. PCT/KR2021/016542, 4 pages.
Wohnsland et al., "High-Throughput Permeability pH Profile and High-Throughput Alkane/Water log P with Artificial Membranes," J. Med. Chem., 2001, pp. 923-930, vol. 44, cited in the Specification.
Office Action dated Feb. 4, 2025 for corresponding Japanese Patent Application No. 2023-528546, along with an English translation (7 pages).
Yumei Cao et al., "Rescue of homeostatic regulation of striatal excitability and locomotor activity in a mouse model of Huntington s disease", Proceedings of the National Academy of Sciences of the United States of America, Feb. 17, 2015, vol. 112, No. 7, pp. 2239-2244, cited in NPL No. 1.

* cited by examiner

Amplex Red

Resorufin

AMINOAROMATIC COMPOUND OR PHARMACEUTICALLY ACCEPTABLE SALT THEREOF, AND PHARMACEUTICAL COMPOSITION FOR PREVENTING OR TREATING NEURODEGENERATIVE DISEASES COMPRISING SAME AS ACTIVE INGREDIENT

CROSS-REFERENCE TO RELATED APPLICATION

The present application is a national stage filing under 35 U.S.C § 371 of PCT application number PCT/KR2021/016542 filed on Nov. 12, 2021 which is based upon and claims the benefit of priorities to Korean Patent Application No. 10-2020-0152267 filed on Nov. 13, 2020 and Korean Patent Application No. 10-2021-0155076 filed on Nov. 11, 2021 in the Korean Intellectual Property Office. All of the aforementioned applications are hereby incorporated by reference in their entireties.

TECHNICAL FIELD

The present invention relates to a novel aminoaromatic compound or a pharmaceutically acceptable salt thereof, and a pharmaceutical composition for preventing or treating neurodegenerative diseases and a health functional food composition for preventing or ameliorating neurodegenerative diseases including the same as an effective component (active ingredient).

BACKGROUND ART

Neurodegenerative diseases are diseases which cause abnormal motor control ability, cognitive dysfunction (impairment), perception dysfunction (perceptual disorders), sensory dysfunction, and autonomic nerve dysfunction due to the decreased function or loss of nerve cells, and a representative example thereof includes Alzheimer's disease (AD), Parkinson's disease (PD), memory impairment, and the like.

One of the main causes of neurodegenerative diseases is oxidative stress of nerve cells due to production of reactive oxygen species (ROS). Oxidative stress is a phenomenon defined as imbalance of antioxidative/oxidative system in vivo, and is known to be produced by an accumulation of reactive oxygen species (ROS) in cells. The oxidative stress as such causes lipid peroxidation, intracellular DNA damage, and the like to induce apoptosis and neuronal death.

In particular, since a brain has high oxygen saturation and is rich in polyunsaturated fatty acid or metal ions which are a direct target for oxidative stress, and neurotransmitters of a brain may undergo auto-oxidation, when the brain is subjected to oxidative stress by reactive oxygen species (ROS), oxidation products to cause neurotoxicity are increased instead of decreasing an unsaturated fatty acid content, and thus, the brain is an organ which is very vulnerable to oxidative stress, and has limited antioxidant and restorative abilities to oxidative stress.

Reactive oxygen species (ROS) are chemically reactive radical species and non-radical species that include oxidative ability, and include a superoxide anion radical ($\cdot O_2^-$), a perhydroxyl radical ($HO_2\cdot$), a hydroxyl radical ($\cdot OH$), singlet oxygen ($^1O_2$), a hydrogen peroxide ($H_2O_2$), an alkoxy radical ($\cdot OR$), a hydroperoxyl radical ($\cdot OOR$), and the like.

Among the reactive oxygen species (ROS), hydrogen peroxide ($H_2O_2$) is the most common product of various oxidation reactions (e.g., oxidative enzyme, dehydrogenases, and peroxidases) which occurs mainly in mitochondria in living organisms. Hydrogen peroxide ($H_2O_2$) which surpasses the by-product itself occurs as both a signal transducer and a toxic molecule. During mitochondrial respiration, a superoxide dismutase (SOD) catalyzes a superoxide anion radical ($\cdot O_2^-$) into hydrogen peroxide ($H_2O_2$) and oxygen ($O_2$).

Another source of the hydrogen peroxide ($H_2O_2$) is nicotinamide adenine dinucleotide phosphate (NADPH) oxidase which catalyzes oxygen ($O_2$) into a superoxide anion radical ($\cdot O_2^-$), resulting in producing hydrogen peroxide ($H_2O_2$). In addition, a xanthine oxidase is responsible for the production of hydrogen peroxide ($H_2O_2$) in a hypoxanthine oxidation process, and a monoamine oxidase (MAO) family member oxidizes monoamine (e.g., dopamine and noradrenaline) and polyamine (e.g., N-acetylputrescine) to produce hydrogen peroxide ($H_2O_2$). Other than that, there are many methods to produce hydrogen peroxide ($H_2O_2$).

An appropriate amount of hydrogen peroxide ($H_2O_2$) is an important second messenger in living organisms since active oxygen (ROS) at a low concentration which is temporarily produced in a specific area by an external signal may regulate cellular functions such as immunity with cell growth and death. However, a large amount of $H_2O_2$ that cannot be regulated by the cellular redox systems can act as a toxic substance within the cell. In other words, $H_2O_2$ can be both beneficial and harmful to health.

An appropriate level of hydrogen peroxide ($H_2O_2$) acts as a cell signaling molecule (CSM) which regulates transcription factors, protein kinases, and growth factors. However, a high level of hydrogen peroxide ($H_2O_2$) damages DNA, lipid, and protein. DNA modification including decomposition of bases, single- or double-stranded DNA breakage, crosslinking with protein, and purine or pyrimidine modification is due to damage by hydrogen peroxide ($H_2O_2$). Hydrogen peroxide ($H_2O_2$) destroys a membrane lipid bilayer by lipid peroxidation which sequentially affects tissue stability, and also causes fragmented proteins, crosslinking of proteins, and amino acid oxidation.

In order to control the change of hydrogen peroxide ($H_2O_2$) level, various antioxidation systems have been established. Catalase (CAT), glutathione peroxidase (GPx), and horseradish peroxidase (HRP) are known hydrogen peroxide ($H_2O_2$) decomposition enzymes. CAT is one of powerful antioxidant enzymes, which contains a heme cofactor and decomposes hydrogen peroxide ($H_2O_2$) into water and oxygen intact. GPx is a selenium cofactor enzyme and hydrogen peroxide ($H_2O_2$) decomposition is accompanied by glutathione (GSH) oxidation. In addition, HRP includes heme as a cofactor, and shows catalase-like activity to reduce hydrogen peroxide ($H_2O_2$) to water and oxygen. All antioxidation systems as such maintain equivalence of a hydrogen peroxide ($H_2O_2$) level in physiological conditions.

However, the balance of hydrogen peroxide ($H_2O_2$) level is often disrupted in pathological conditions, and this is closely related to pathology. In general, in neurodegenerative diseases, tumors, and autoimmune diseases, the balance of hydrogen peroxide ($H_2O_2$) tilts to an excessive level. For example, accumulation of amyloid-beta induces proliferation of reactive astrocyte and monoamine oxidase B (MAO-B).

Therefore, prevention of oxidative stress due to hydrogen peroxide ($H_2O_2$) is emerging as a therapeutic strategy.

However, an effective drug target for preventing damage due to hydrogen peroxide ($H_2O_2$) has not been determined yet.

DISCLOSURE

Technical Problem

While studying to discover a novel compound having an effect of preventing or treating neurodegenerative diseases, the present inventors conceived that the level of hydrogen peroxide which is one of reactive oxygen species is significantly high in pathological conditions such as neurodegenerative diseases, such as, in particular, Alzheimer's disease, as compared with the case of being by-produced by an endogenous oxidation reaction such as mitochondrial respiration, and intended to develop a novel compound which acts as a scavenger against hydrogen peroxide which is one of various active oxygen species. As a result, we found that specific aminoaromatic compounds removes only hydrogen peroxide, not a hydroxyl radical, and completed the present invention.

An object of the present invention is to provide a novel aminoaromatic compound which is useful as a blood hydrogen peroxide scavenger or a pharmaceutically acceptable salt thereof.

Another object of the present invention is to provide a pharmaceutical composition for preventing or treating neurodegenerative diseases, including the novel aminoaromatic compound of the present invention or the pharmaceutically acceptable salt thereof as an effective component.

Still another object of the present invention is to provide a health functional food composition for preventing or ameliorating neurodegenerative diseases, including the novel aminoaromatic compound of the present invention or a sitologically acceptable salt thereof as an effective component.

Technical Solution

In order to achieve the above objects, in one general aspect, an aminoaromatic compound represented by the following Chemical Formula 1 or a pharmaceutically acceptable salt thereof is provided:

[Chemical Formula 1]

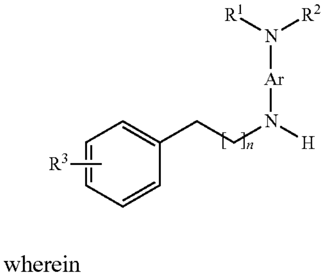

wherein

Ar is $C_6$-$C_{20}$ arylene, and the arylene of Ar may be further substituted by one or more selected from $C_1$-$C_{10}$ alkyl, $C_1$-$C_{10}$ alkoxy, amino, mono- or di-$C_1$-$C_{10}$ alkylamino, halo$C_1$-$C_{10}$ alkyl, and halo$C_1$-$C_{10}$ alkoxy and hydroxy;

$R^1$ and $R^2$ are independently of each other hydrogen or $C_1$-$C_{10}$ alkyl;

$R^3$ is halogen, $C_1$-$C_{10}$ alkoxy, halo$C_1$-$C_{10}$ alkyl, or halo$C_1$-$C_{10}$ alkoxy; and n is an integer of 1 or 2;

provided that $R^3$ is halogen, n is an integer of 1.

In another general aspect, a pharmaceutical composition for preventing or treating neurodegenerative disease includes: the aminoaromatic compound represented by Chemical Formula 1 or a pharmaceutically acceptable salt thereof as an effective component.

In still another general aspect, a health functional food composition for preventing or ameliorating neurodegenerative disease includes: the aminoaromatic compound represented by Chemical Formula 1 or a sitologically acceptable salt thereof as an effective component.

Advantageous Effects

The aminoaromatic compound according to the present invention acts as a scavenger to remove hydrogen peroxide which is a kind of reactive oxygen.

The aminoaromatic compound according to the present invention scavenges hydrogen peroxide which is an intracellular reactive oxygen species (ROS), thereby inhibiting apoptosis by $H_2O_2$-induced oxidative stress.

That is, since the aminoaromatic compound according to the present invention acts with a heme-containing enzyme to lower a $H_2O_2$ concentration, it does not excessively lower the $H_2O_2$ concentration, but removes overproduced hydrogen peroxide so that the $H_2O_2$ concentration is appropriate at a level required in vivo.

The aminoaromatic compound according to the present invention is a small molecule blood hydrogen peroxide scavenger and has very high blood-brain barrier (BBB) permeability and acts directly on the brain, thereby showing an excellent effect on brain disease treatment.

The aminoaromatic compound according to the present invention shows a hydrogen peroxide scavenging activity and improves apoptosis induced by hydrogen peroxide, thereby showing antioxidant properties to ameliorate cognitive and memory impairments.

The aminoaromatic compound according to the present invention decomposes hydrogen peroxide in the presence of a heme-containing peroxidase, hemoglobin (Hb) present in the body to lower a blood hydrogen peroxide level, resulting in inhibiting or treating onset of neurodegenerative diseases.

Therefore, the aminoaromatic compound according to the present invention inhibits damage caused by harmful hydrogen peroxide, and thus, may be used as an effective component of a pharmaceutical composition for preventing or treating neurodegenerative disease and a health functional food composition for preventing or ameliorating neurodegenerative diseases.

[(A) a graph showing a $H_2O_2$ decomposition effect by an aminoaromatic compound of the present invention, KDS12008 (Example 1) (10 μM) and sodium pyruvate (10 mM); (B) the results of cell viability test of the aminoaromatic compound of the present invention, KDS12008 (Example 1) (100 μM) and sodium pyruvate (10 mM). The fluorescence intensity represents an amount of $H_2O_2$ in cells, which was normalized by control conditions. P<0.01; *P<0.001; ns, non-significant.].

Figure 4:
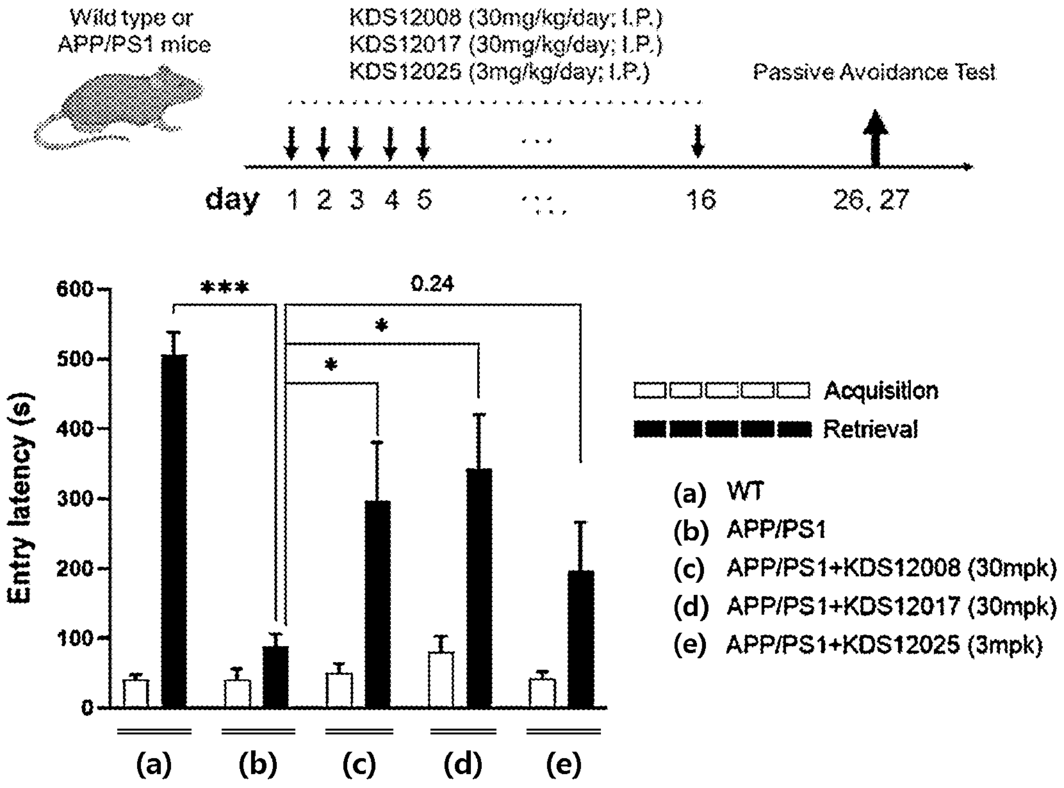

FIG. 4—the results of a recovery experiment of memory loss (memory impairment) of an APP/PS1 mouse treated with the aminoaromatic compound of the present invention in Experimental Example 3 [(A) a schematic timeline of drug treatment and passive avoidance test (PAT); (B) a bar graph showing latency in a dark room in a passive avoidance test of a mouse treated with the aminoaromatic compound of the present invention, KDS12008 (Example 1), KDS12017 (Example 16), or KDS12025 (Example 21), respectively. Data is indicated as average±SEM. Unpaired two-tailed t-test. *P<0.05, ****P<0.0001.].

Figure 5:
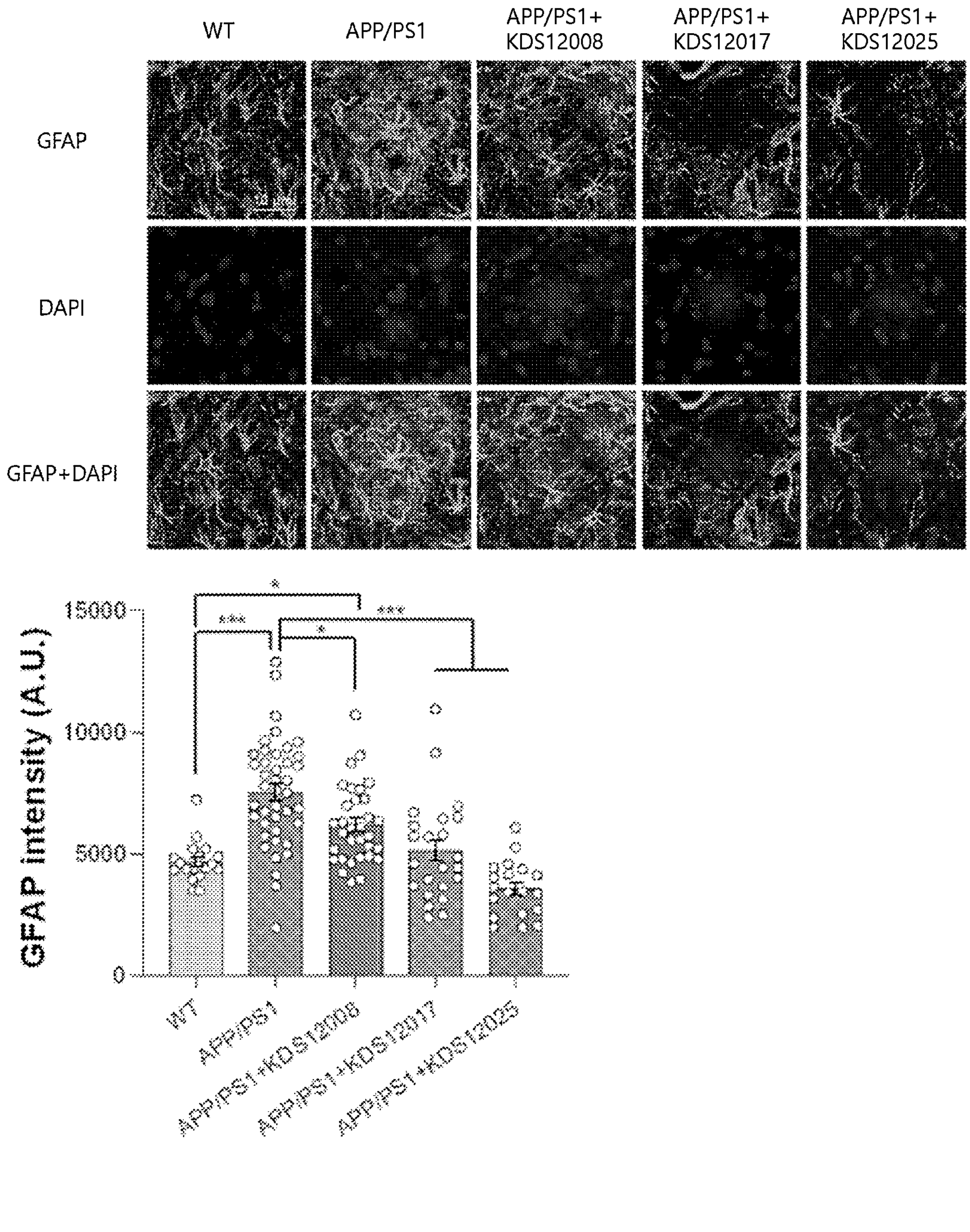

FIG. 5—the results of immunohistochemistry (IHC) I of an APP/PS1 mouse brain tissue treated with the aminoaromatic compound of the present invention, KDS12008 (Example 1), KDS12017 (Example 16), or KDS12025 (Example 21), respectively in Experimental Example 4.

Figure 6:
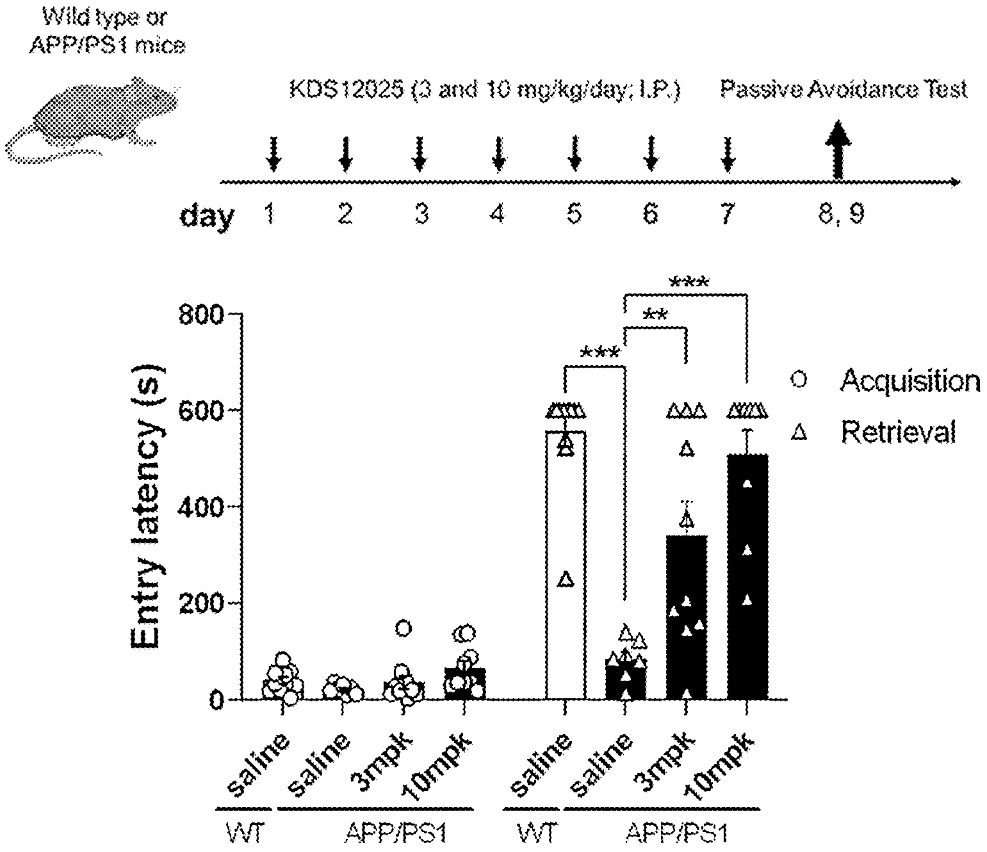

FIG. 6—the results of the passive avoidance test (PAT) of Experimental Example 5.

Figure 7:
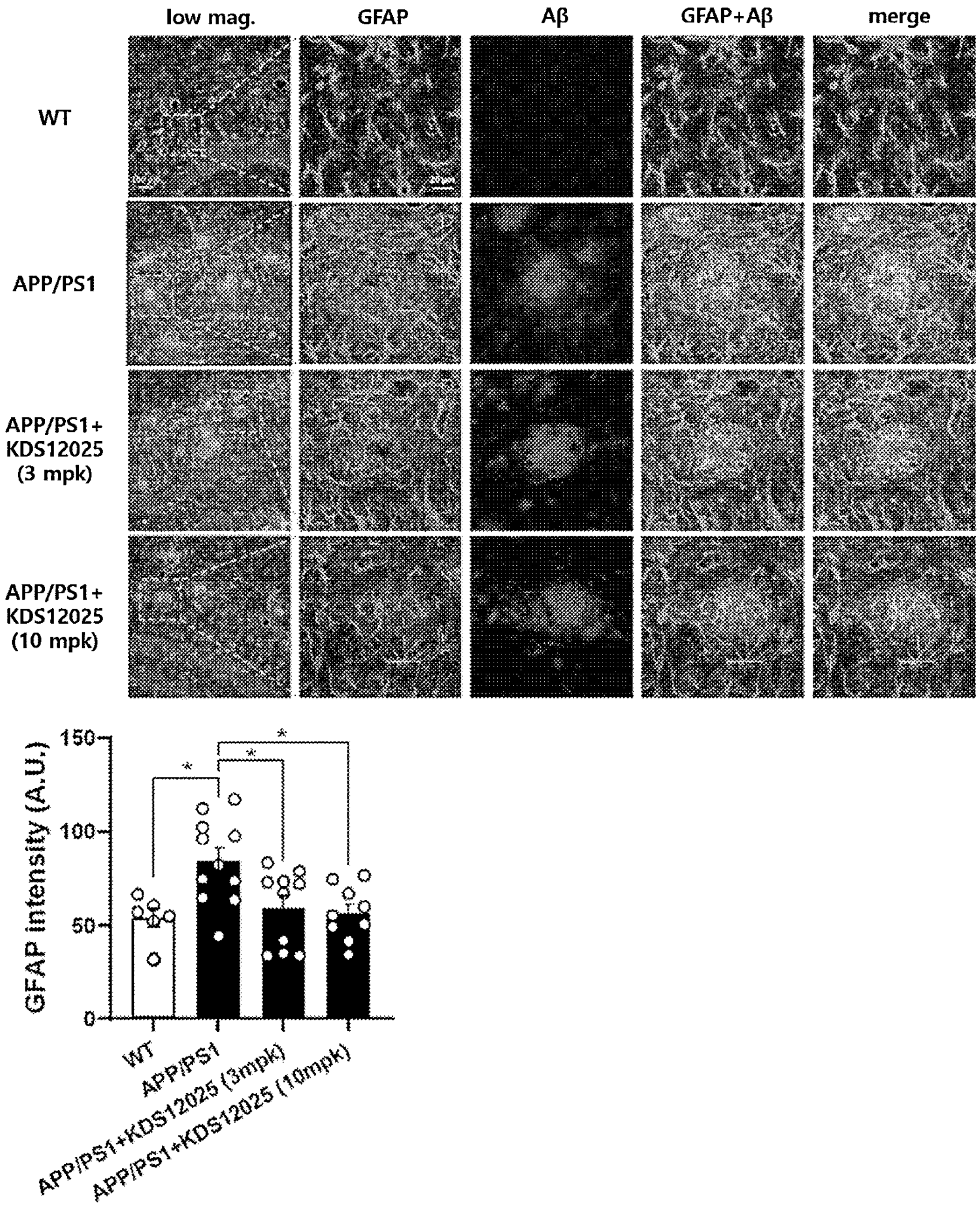

FIG. 7—the results of immunohistochemistry (IHC) II of a brain tissue of Experimental Example 6.

Figure 8:
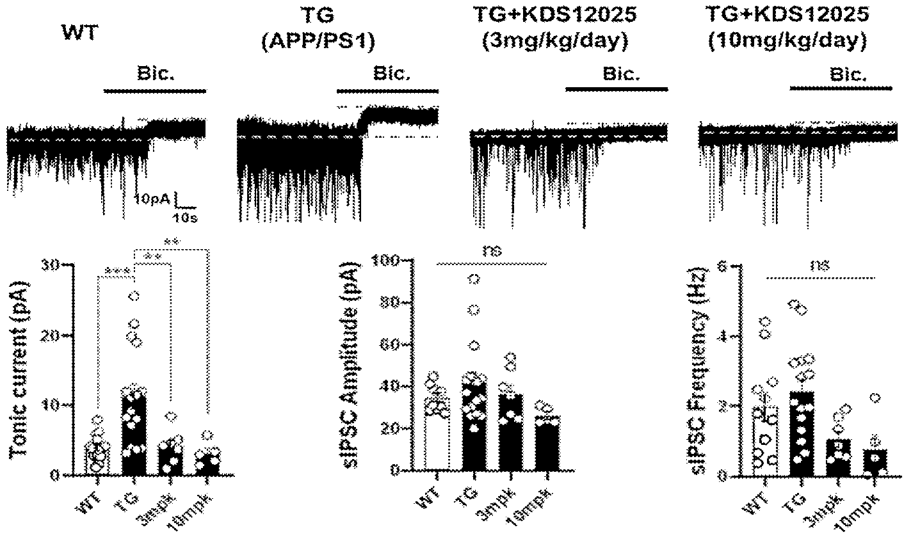

FIG. 8—the results of the electrophysiology of Experimental Example 7.

Figure 9:
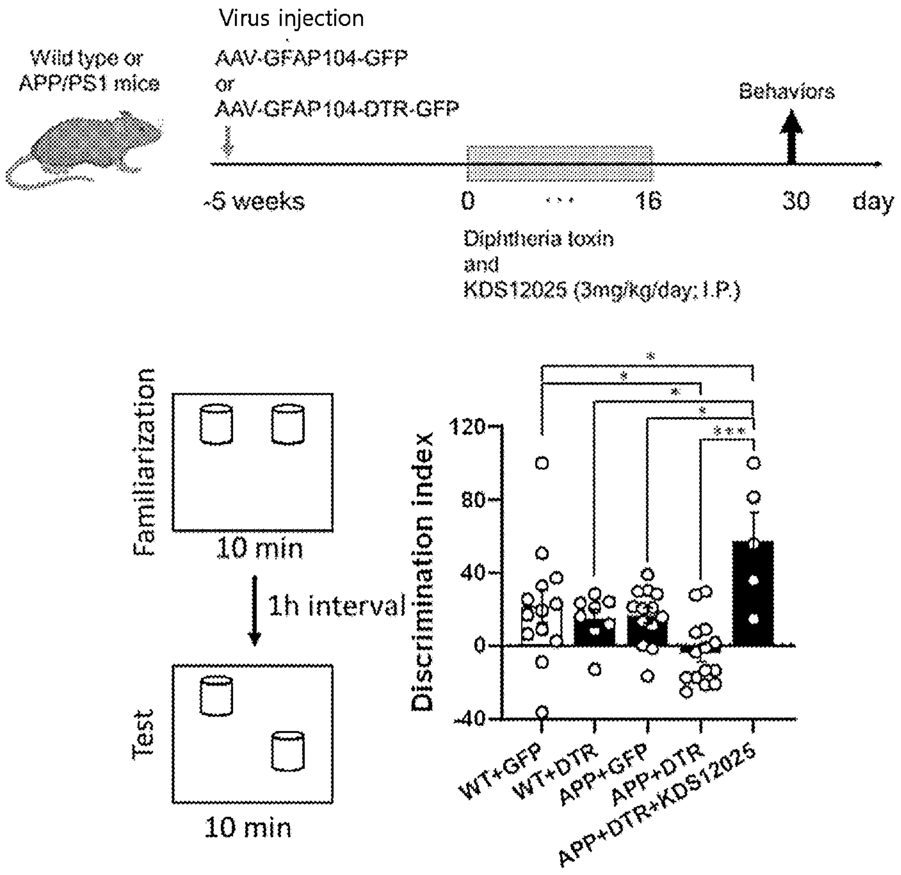

FIG. 9—the results of a novel place recognition experiment of Experimental Example 8.

Figure 10:
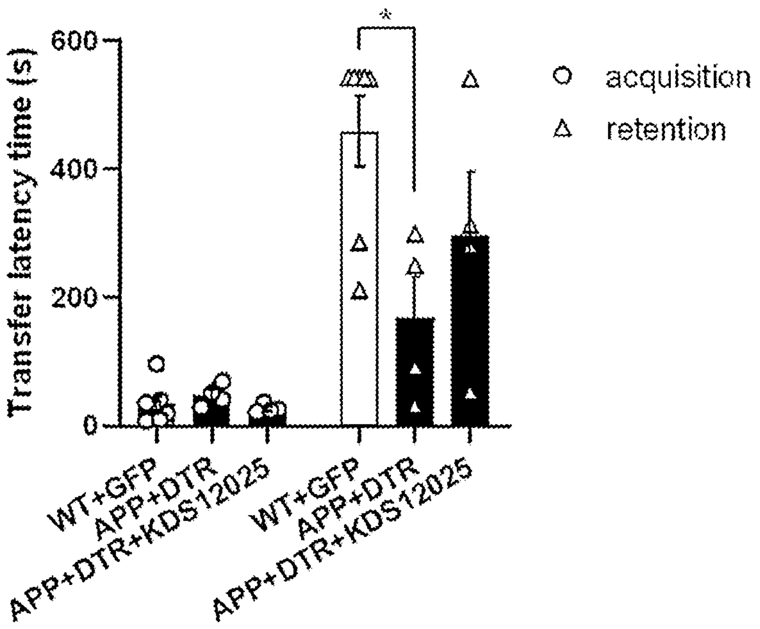

FIG. 10—the results of the passive avoidance test (PAT) of Experimental Example 8.

Figure 11:
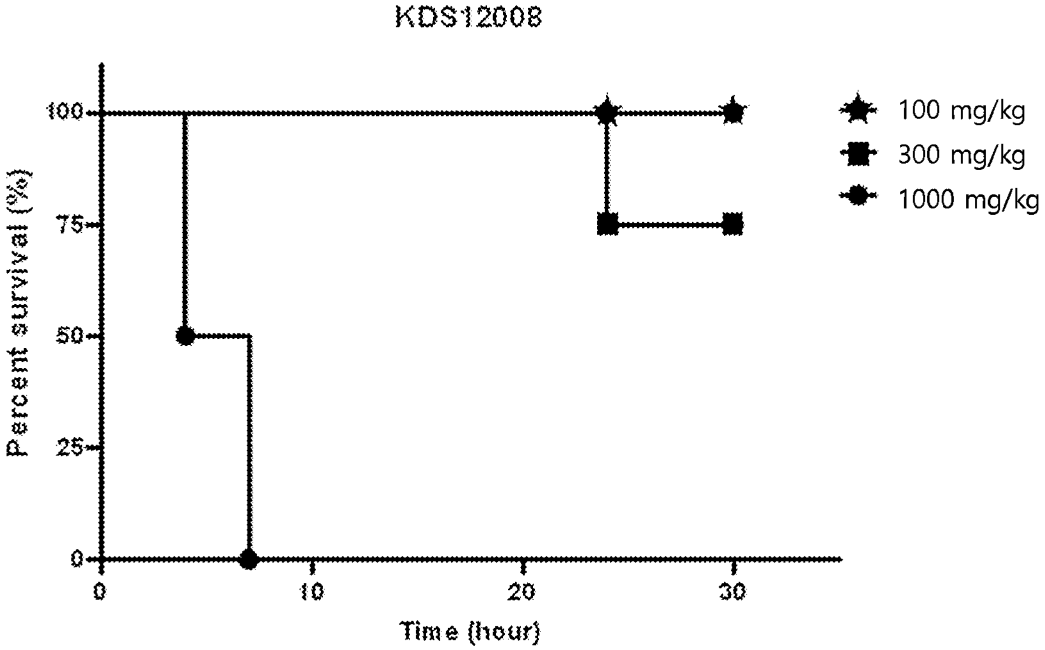
Figure 12:
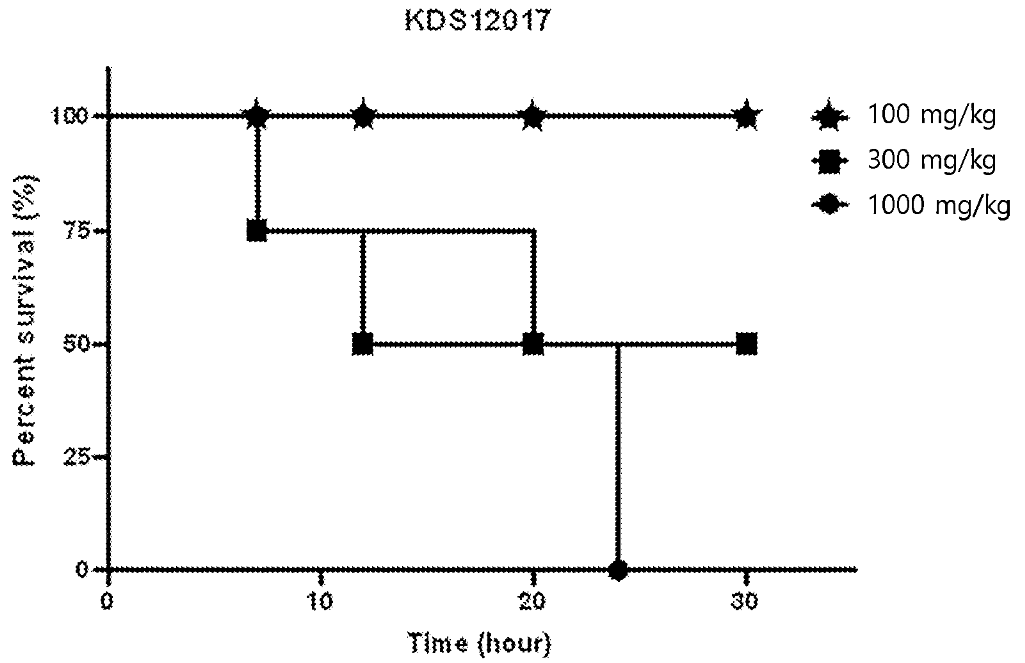
Figure 13:
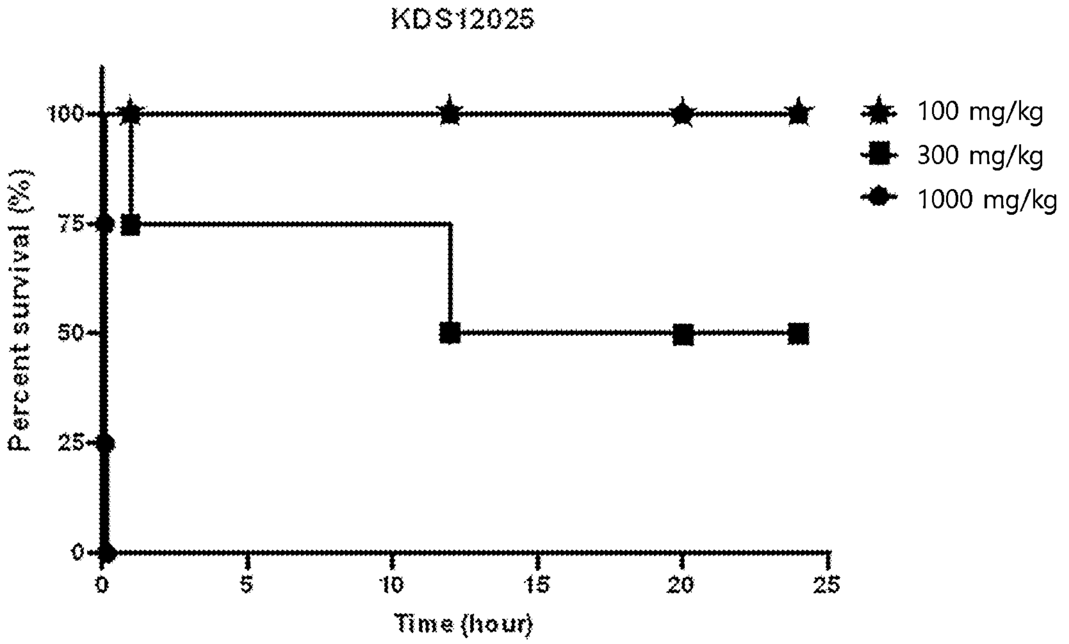

FIGS. 11 to 13—the results of single toxicity assessment (lethal dose 50, LD50) of Experimental Example 9.

BEST MODE

Hereinafter, the novel aminoaromatic compound of the present invention or a pharmaceutically acceptable salt thereof will be described in detail. Herein, technical terms and scientific terms used in the present specification have the general meaning understood by those skilled in the art to which the present invention pertains unless otherwise defined, and description for the known function and configuration which may unnecessarily obscure the gist of the present invention will be omitted in the following description.

The following terms used in the present specification are defined as follows, but they are only illustrative and do not limit the present invention, application, or use.

In the present specification, the terms "substituent", "radical", "group", "moiety", and "fragment" may be used interchangeably.

In the present specification, the term "$C_A$-$C_B$" refers to "the number of carbons being A or more and B or less".

In the present specification, the term "alkyl" refers to a monovalent straight chain or branched chain saturated hydrocarbon radical composed of only carbon and hydrogen atoms. The alkyl may have 1 to 10, 1 to 7, or 1 to 4 carbon atoms. "Lower alkyl" refers to straight chain or branched chain alkyl having 1 to 4 carbon atoms. As an example, the alkyl includes methyl, ethyl, propyl, isopropyl, butyl, isobutyl, t-butyl, pentyl, hexyl, ethylhexyl, and the like, but is not limited thereto.

In the present specification, the term "arylene" refers to a divalent organic radical of an aromatic ring derived from aromatic hydrocarbon by removal of two hydrogen atoms, including a single- or fused ring system containing appropriately 4 to 7, preferably 5 or 6 ring atoms in each ring, and even a form in which a plurality of aryls are connected by a single bond. A specific example thereof includes phenylene, naphthylene, biphenylene, anthrylene, and the like, but is not limited thereto.

In the present specification, the term "alkoxy" is a —O—alkyl radical, in which "alkyl" is as defined above. A specific example thereof includes methoxy, ethoxy, isopropoxy, butoxy, isobutoxy, t-butoxy, and the like, but is not limited thereto.

In the present specification, the term "halo" or "halogen" refers to a halogen group element, and for example, includes fluoro, chloro, bromo, and iodo.

In the present specification, the term "haloalkyl" or "haloalkoxy" refers to an alkyl or alkoxy group in which one or more hydrogen atoms are substituted with a halogen atom, respectively, wherein alkyl and halogen are as defined above. For example, haloalkyl may be fluoromethyl, difluoromethyl, trifluoromethyl, fluoroethyl, difluoroethyl, perfluoroethyl, and the like, and haloalkoxy may be fluoromethoxy, difluoromethoxy, trifluoromethoxy, fluoroethoxy, difluoroethoxy, perfluoroethoxy, and the like.

In the present specification, the term "amino" refers to —$NH_2$, and "hydroxy" refers to —OH.

In the present specification, the term "alkylamino" refers to an amino radical in which one or two alkyls are substituted, and a specific example thereof includes methylamino (—NHMe), dimethylamino (—$NMe_2$), ethylamino (—NHEt), diethylamino (—$NEt_2$), and the like, but is not limited thereto.

In the present specification, the term "pharmaceutically acceptable" represents non-toxic properties in individuals such as cells or humans exposed to the composition, means that it is appropriate for use as a pharmaceutical preparation, is generally regarded as being safe for the use, and means that it is officially approved by the national management agency or listed in the Korean Pharmacopoeia or the US Pharmacopoeia.

In the present specification, the term "pharmaceutically acceptable salt" refers to any organic or inorganic addition salt of the compound of the present invention, in which the side effect caused by the salt does not reduce advantageous efficacy of the compound of the present invention itself at a concentration having a relatively non-toxic and harmless effective action to a patient.

In the present specification, the term "pharmaceutically acceptable excipient" and "pharmaceutically acceptable carrier" refer to materials which aid administration of an activator and absorption by a subject.

In the present specification, the term "oxidative stress" is used according to common sense and refers to an abnormal level of a reactive oxygen species.

In the present specification, the term "prevention" refers to all actions of inhibiting or delaying occurrence, spread, and recurrence of neurodegenerative diseases.

In the present specification, the term "amelioration" refers to all actions of at least decreasing parameters related to the conditions to be treated, for example, the severity of symptoms.

In the present specification, the term "treatment" refers to all actions of ameliorating or beneficially altering the symptoms of neurodegenerative diseases.

In the present specification, the term "individual" refers to all animals including humans who have or are likely to develop neurodegenerative diseases. The animals may be mammals such as cattle, horses, sheep, pigs, coats, camels, antelopes, dogs, and cats in need of treatment of similar symptoms, as well as humans, but are not limited thereto.

In the present specification, the term "administration" means that the pharmaceutical composition of the present invention is introduced to an individual by any appropriate method, and the administration route of the composition of the present invention may be various, such as oral or parenteral, as long as the composition may reach a target tissue.

In the present specification, the term "pharmaceutically effective amount" refers to an amount which is sufficient to treat a disease at a reasonable benefit/risk ratio applicable to medical treatment and does not cause side effects, and an effective dose level may be easily determined by a person skilled in the art according to factors including patients' gender, age, weight, and health state, the kind of diseases, severity, an activity of a drug, a sensitivity to a drug, an administration manner, an administration time, administration route and releasing rate, a treatment period, formulation, or a simultaneously used drug, and other factors well known in the medical field.

In the present specification, the term "food" may be meat, sausage, bread, chocolate, candy, snacks, confectionery, pizza, ramen, other noodles, chewing gum, dairy products including ice cream, various soups, beverages, tea, drinks, alcoholic beverages, vitamin complexes, health functional food, health food, and the like, and includes all food in a common sense.

In the present specification, the term "health functional food" refers to food manufactured and processed using raw materials or components having functionality useful to the human body in accordance with Functional Foods for Health Act No. 6727, and "functional" refers to regulating nutrients for the structure and function of the human body or intake for the purpose of obtaining a beneficial effect for health applications such as physiological action.

In the present specification, the term "sitologically acceptable salt" refers to a formulation of a compound, which does not cause serious irritation to an organism to which a compound is administered and does not damage the biological activity and physical properties of the compound.

The present invention provides a novel aminoaromatic compound represented by the following Chemical Formula 1 or a pharmaceutically acceptable salt thereof, which is useful as a blood hydrogen peroxide scavenger:

[Chemical Formula 1]

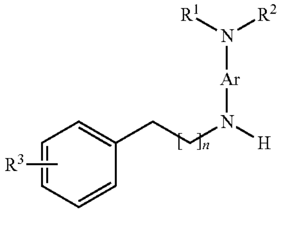

wherein

Ar is $C_6$-$C_{20}$ arylene, and the arylene of Ar may be further substituted by one or more selected from $C_1$-$C_{10}$ alkyl, $C_1$-$C_{10}$ alkoxy, amino, mono- or di-$C_1$-$C_{10}$ alkylamino, halo$C_1$-$C_{10}$ alkyl, and halo$C_1$-$C_{10}$ alkoxy and hydroxy;

$R^1$ and $R^2$ are independently of each other hydrogen or $C_1$-$C_{10}$ alkyl;

$R^3$ is halogen, $C_1$-$C_{10}$ alkoxy, halo$C_1$-$C_{10}$ alkyl, or halo$C_1$-$C_{10}$ alkoxy; and n is an integer of 1 or 2;

provided that $R^3$ is halogen, n is an integer of 1.

The aminoaromatic compound according to the present invention has low cytotoxicity and is a small molecule compound, and may act as a scavenger to remove hydrogen peroxide which is a kind of reactive oxygen.

The aminoaromatic compound according to the present invention does not remove a hydroxyl radical and is not a MAO-B inhibitor. As a result of ROS-GLO analysis, the aminoaromatic compound according to the present invention was confirmed to act as a catalyst of a reaction of decomposing hydrogen peroxide into water in the presence of endogenous peroxidase, in particular, heme-containing peroxidase, hemoglobin (Hb).

That is, since the aminoaromatic compound according to the present invention acts with the heme-containing peroxidase, hemoglobin (Hb) present in vivo to remove overproduced hydrogen peroxide to an appropriate level of concentration, the aminoaromatic compound of the present invention inhibits death of nerve cells due to harmful hydrogen peroxide, and thus, may be useful for prevention, amelioration, or treatment of neurodegenerative diseases. In addition, the aminoaromatic compound according to the present invention has a function to penetrate a blood brain barrier (BBB) with excellent efficiency, and thus, a fast, rapid, and more efficient therapeutic effect may be obtained with administration of a low content.

In an exemplary embodiment of the present invention, the Ar may be $C_6$-$C_{12}$ arylene, preferably phenylene or biphenylene; and Ar may be further substituted with one or more selected from $C_1$-$C_7$ alkyl, $C_1$-$C_7$ alkoxy, amino, and hydroxy.

In an exemplary embodiment of the present invention, the Ar may be phenylene, and preferably, a nitrogen atom may be introduced to positions 1 and 4 of the phenylene, respectively.

The aminoaromatic compound according to an exemplary embodiment of the present invention may be specifically represented by the following Chemical Formula 2 or 3:

The aminoaromatic compound according to an exemplary embodiment of the present invention may be specifically represented by the following Chemical Formula 2 or 3:

[Chemical Formula 2]

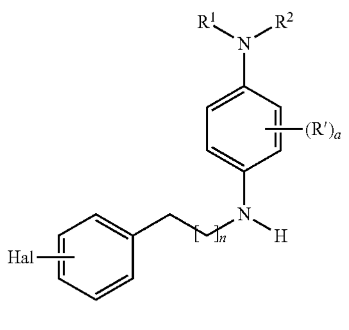

-continued

[Chemical Formula 3]

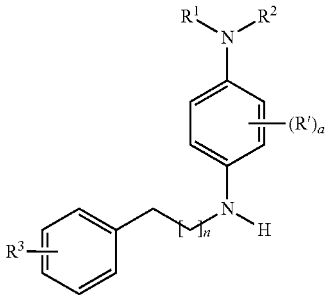

wherein $R^1$ and $R^2$ are independently of each other hydrogen or $C_1$-$C_7$ alkyl;

Hal is halogen;

$R^3$ is $C_1$-$C_7$ alkoxy or halo$C_1$-$C_7$ alkyl;

R' is $C_1$-$C_7$ alkyl, $C_1$-$C_7$ alkoxy, amino, or hydroxy;

a is an integer of 0 to 4; and n is an integer of 1 or 2.

Preferably, in Chemical Formula 2 and 3 according to an exemplary embodiment of the present invention, $R^1$ and $R^2$ may be independently of each other hydrogen or $C_1$-$C_4$ alkyl; Hal may be halogen; $R^3$ may be $C_1$-$C_4$ alkoxy or halo$C_1$-$C_4$ alkyl; a may be an integer of 0; and n may be an integer of 1 or 2.

Chemical Formula 2 according to an exemplary embodiment may be represented by the following Chemical Formula 4:

[Chemical Formula 4]

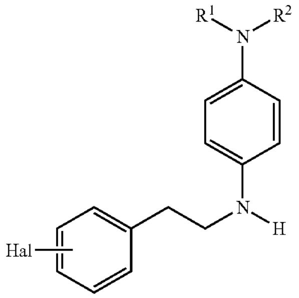

wherein $R^1$ and $R^2$ are independently of each other hydrogen or $C_1$-$C_4$ alkyl; and Hal is halogen.

Specifically, in Chemical Formula 4, $R^1$ and $R^2$ may be independently of each other $C_1$-$C_4$ alkyl; and Hal may be halogen.

Specifically, in Chemical Formula 4, $R^1$ may be hydrogen; $R^2$ may be $C_1$-$C_4$ alkyl; and Hal may be halogen.

Specifically, in Chemical Formula 4, $R^1$ and $R^2$ may be independently of each other hydrogen; and Hal may be halogen.

Chemical Formula 3 according to an exemplary embodiment may be represented by the following Chemical Formula 5:

[Chemical Formula 5]

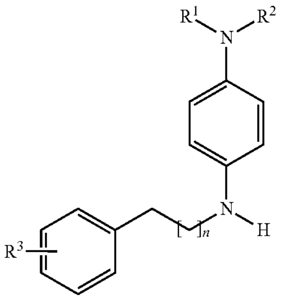

wherein $R^1$ and $R^2$ are independently of each other hydrogen or $C_1$-$C_4$ alkyl;

$R^3$ is $C_1$-$C_4$ alkoxy or halo$C_1$-$C_4$ alkyl; and n is an integer of 1 or 2.

Specifically, in Chemical Formula 5, $R^1$ and $R^2$ may be independently of each other $C_1$-$C_4$ alkyl; $R^3$ may be $C_1$-$C_4$ alkoxy or halo$C_1$-$C_4$ alkyl; and n may be an integer of 1 or 2.

Specifically, in Chemical Formula 5, $R^1$ may be hydrogen; $R^2$ may be $C_1$-$C_4$ alkyl; $R^3$ may be $C_1$-$C_4$ alkoxy or halo$C_1$-$C_4$ alkyl; and n may be an integer of 1 or 2.

Specifically, in Chemical Formula 5, $R^1$ and $R^2$ may be independently of each other hydrogen; $R^3$ may be halo$C_1$-$C_4$ alkyl; and n may be an integer of 1 or 2.

In any compound described in the present specification, halogen or halo may be fluorine.

The aminoaromatic compound according to an exemplary embodiment may be any one selected from the following compound group, and is not limited thereto:

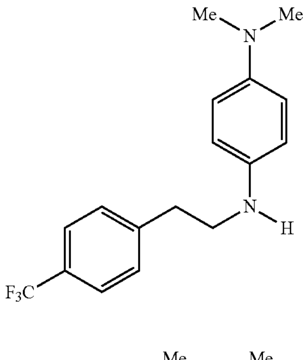

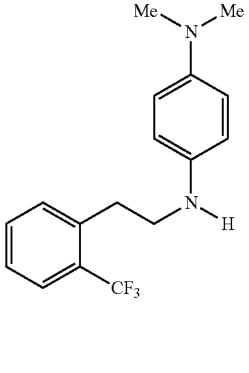

-continued
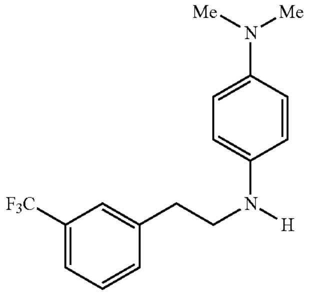
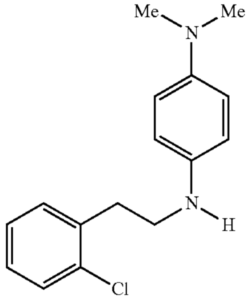
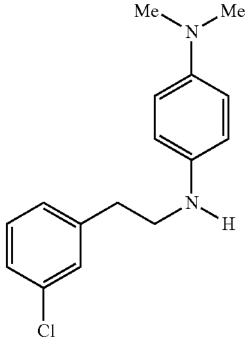
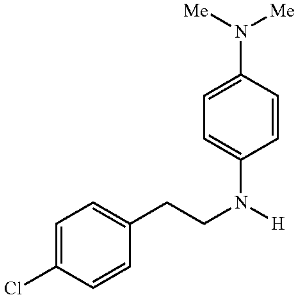
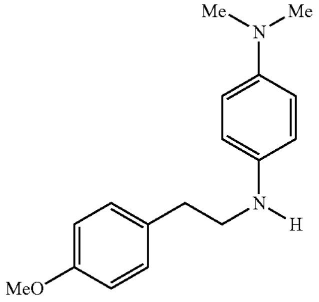
-continued
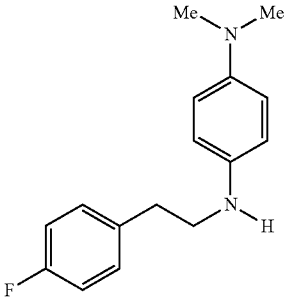
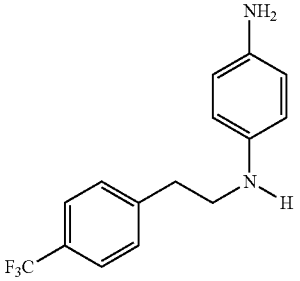
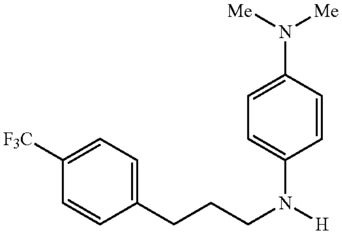
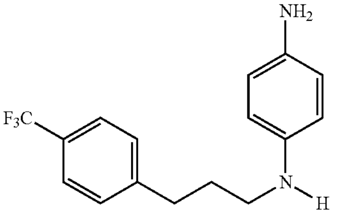
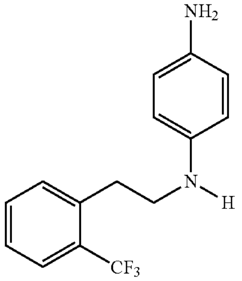
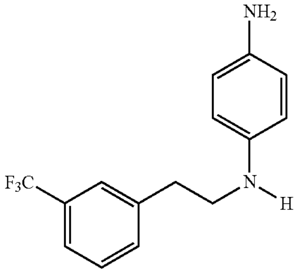

-continued

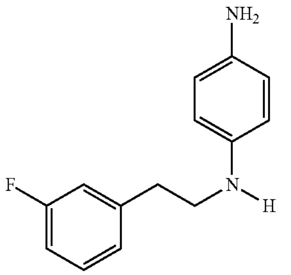

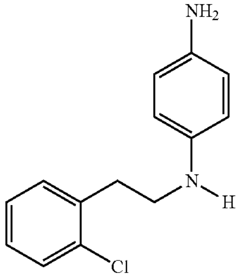

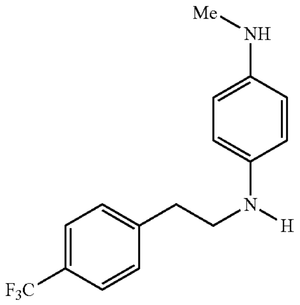

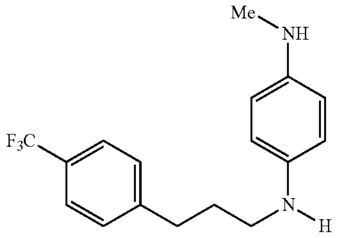

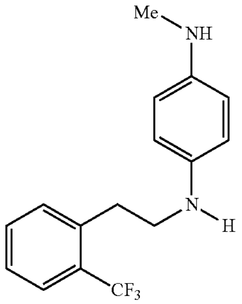

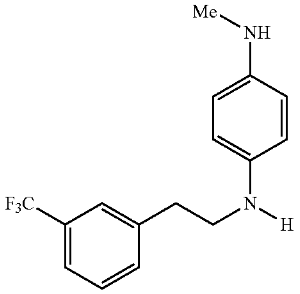

-continued

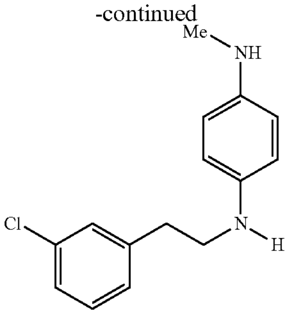

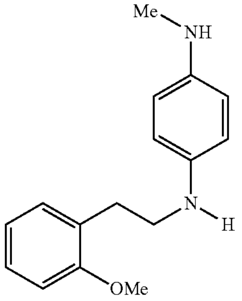

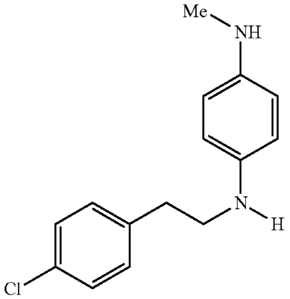

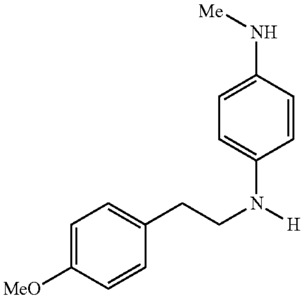

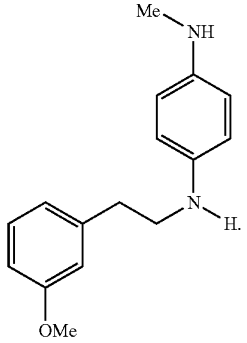

It will be apparent to a person skilled in the art that the method of preparing an aminoaromatic compound according to an exemplary embodiment of the present invention may be performed using a method known in the art or by appropriately changing the method. In addition, a reaction time in the method of preparing the compound of Chemical Formula 1 according to an exemplary embodiment of the present invention may vary depending on the kind of reaction material and solvent and the amount of solvent, and as an example, the reaction is completed after confirming that the starting material is completely consumed by TLC and the like. When the reaction is completed, the solvent is distilled under reduced pressure, and then a target may be separated and purified by a common method such as column chromatography. As an example, the compound may be prepared by reacting an arylenediamine compound and a phenyl alkyl bromide compound, and more details are described in the following examples.

[Reaction Formula 1]

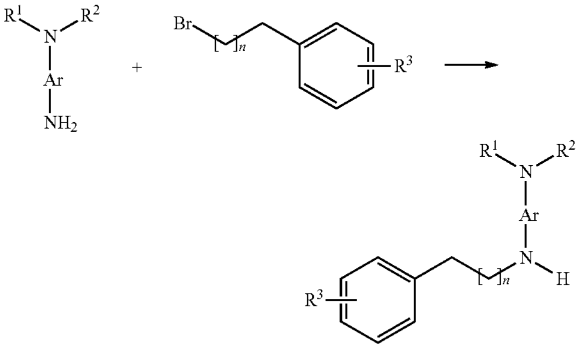

1 wherein Ar, $R^1$, $R^2$, $R^3$, and n are as defined in Chemical Formula 1.

The present invention includes not only the aminoaromatic compound and the pharmaceutically acceptable salt thereof, but also all possible prodrugs, hydrates, and solvates which may be prepared therefrom.

That is, since the aminoaromatic compound of the present invention may be used in the form of a prodrug, a hydrate, a solvate, and a pharmaceutically acceptable salt for enhancing in-vivo absorption or increasing solubility, the prodrug, the hydrate, the solvate, and the pharmaceutically acceptable salt also belong to the scope of the present invention.

The aminoaromatic compound of the present invention may be used in the form of a pharmaceutically acceptable salt, and the pharmaceutically acceptable salt is a salt prepared according to a common method in the art, and the preparation method thereof is known to a person skilled in the art. Specifically, the pharmaceutically acceptable salt includes salts derived from the following free acids and bases which are pharmacologically or physiologically acceptable, but is not limited thereto.

An acid addition salt formed by the pharmaceutically acceptable free acid is obtained from inorganic acids such as hydrochloric acid, nitric acid, phosphoric acid, sulfuric acid, hydrobromic acid, hydroiodic acid, nitrous acid, and phosphorous acid, and organic acids such as methanesulfonic acid, p-toluenesulfonic acid, acetic acid, trifluoroacetic acid, maleic acid, succinic acid, oxalic acid, benzoic acid, tartaric acid, fumaric acid, manderic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, and hydroiodic acid. The kind of pharmaceutically non-toxic salts as such includes sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate, mandelate, and the like.

The acid addition salt may be prepared by a common method, and for example, may be prepared by dissolving the aminoaromatic compound of the present invention in a water miscible organic solvent such as methanol, ethanol, acetone, dichloromethane, and acetonitrile, adding an organic acid or inorganic acid to produce a precipitate, and filtering and drying the precipitate, or by distilling a solvent and an excessive amount of acid under reduced pressure, performing drying, and performing crystallization under an organic solvent.

In addition, a pharmaceutically acceptable metal salt may be prepared using a base. An alkali metal salt or an alkali earth metal salt is obtained by, for example, dissolving the aminoaromatic compound of the present invention in an excessive amount of an alkali metal hydroxide or alkali earth metal hydroxide solution, filtering the undissolved aminoaromatic compound, and then evaporating and drying a filtrate. Herein, it is pharmaceutically appropriate to prepare a sodium, potassium, or calcium salt as a metal salt, but which is not limited thereto. In addition, a silver salt corresponding thereto may be obtained by reacting the alkali metal or alkali earth metal salt with an appropriate silver salt (e.g., silver nitrate).

Preferably, the pharmaceutically acceptable salt of the aminoaromatic compound according to an exemplary embodiment of the present invention may be a hydrochloride.

That is, the aminoaromatic compound according to an exemplary embodiment of the present invention may be a compound in the form of hydrochloride selected from the following structures:

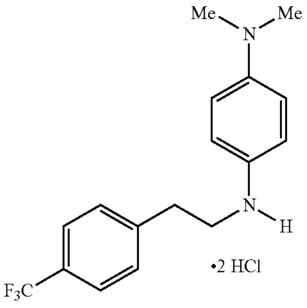

•2 HCl

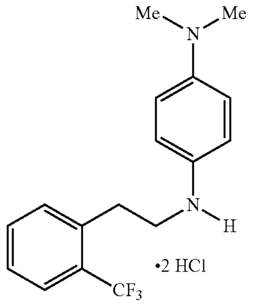

•2 HCl

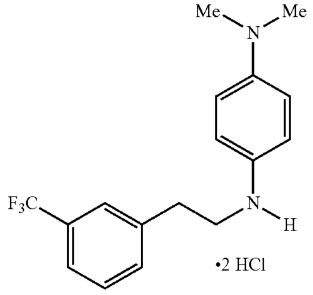

•2 HCl

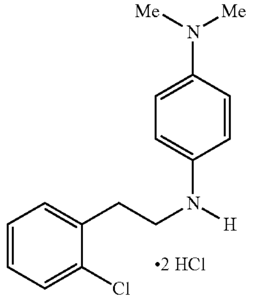

•2 HCl

-continued
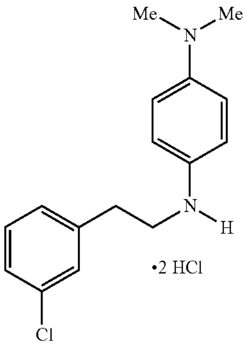
•2 HCl
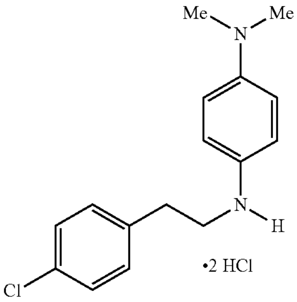
•2 HCl
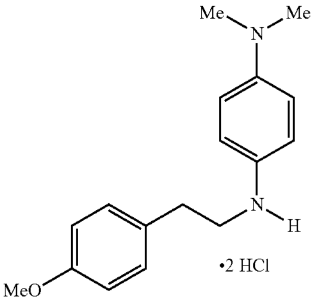
•2 HCl
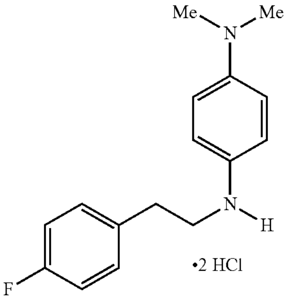
•2 HCl
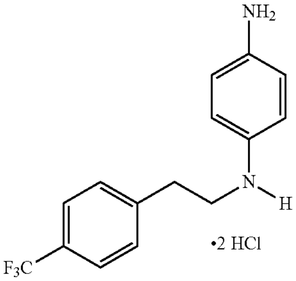
•2 HCl
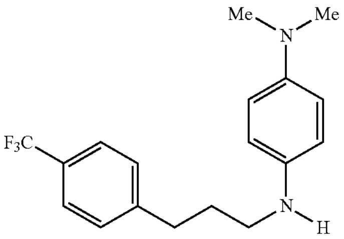
•2 HCl
-continued
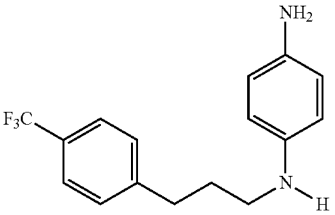
•2 HCl
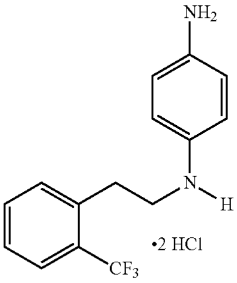
•2 HCl
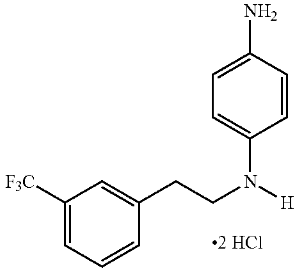
•2 HCl
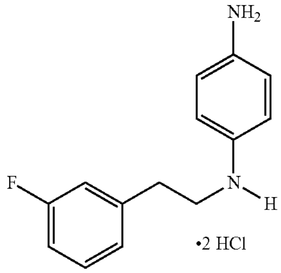
•2 HCl
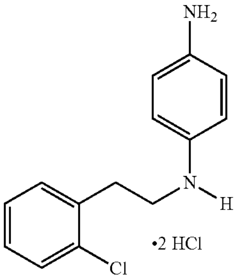
•2 HCl
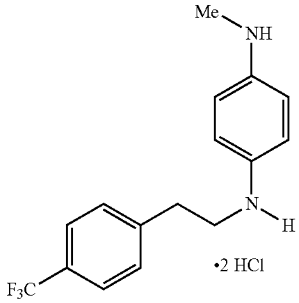
•2 HCl
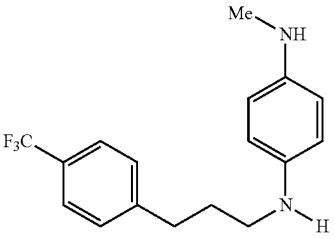
•2 HCl
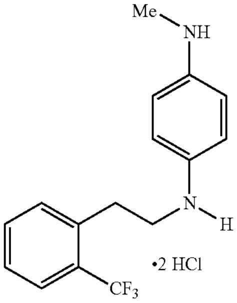
•2 HCl
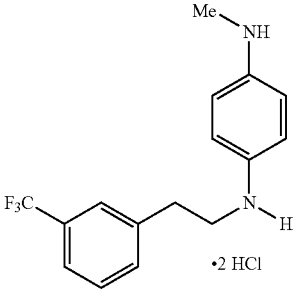
•2 HCl -continued

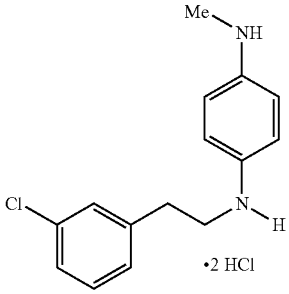

•2 HCl

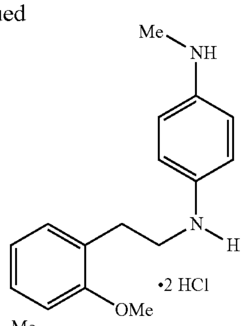

•2 HCl

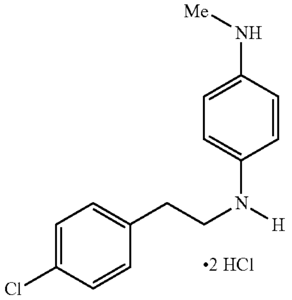

•2 HCl

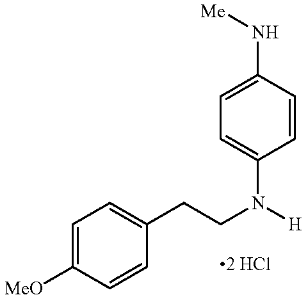

•2 HCl

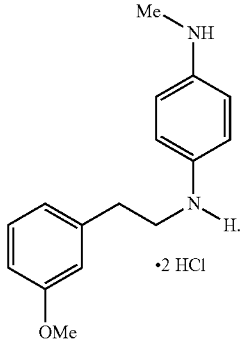

•2 HCl

The hydrate of the aminoaromatic compound of the present invention refers to the aminoaromatic compound of the present invention or the pharmaceutically acceptable salt thereof including a stoichiometric or non-stoichiometric amount of water bonded by a non-covalent intermolecular force.

The solvate of the aminoaromatic compound of the present invention refers to the aminoaromatic compound or a pharmaceutically acceptable salt thereof which includes a stoichiometric or non-stoichiometric amount of solvent bonded by a non-covalent intermolecular force. An available solvent includes a volatile and non-toxic solvent.

The aminoaromatic compound of the present invention may be administered in the form of a prodrug which is decomposed in the human or animal body to provide the compound of the present invention as an effective component. The prodrug may be used for modifying and/or improving a physical and/or pharmacokinetic profile of a parent compound, and may be formed when the parent compound contains an appropriate group or substituent for deriving formation of the prodrug.

If any compound (prodrug) is separated in vivo and produces the aminoaromatic compound of the present invention or the salt thereof, the compound also belongs to the scope of the present invention. When it is used in the present specification and not indicated otherwise, the term "prodrug" refers to the compound of the present invention which may be hydrolyzed, oxidized, and react differently under biological conditions (in vitro or in vivo) for supplying an active compound, in particular, the compound of the present invention. The examples of the prodrug include compounds which are biohydrolyzed to produce the compound of the present invention, including a biohydrolyzable part such as biohydrolyzable amides, biohydrolyzable esters, biohydrolyzable carbamates, biohydrolyzable carbonates, biohydrolyzable ureides, and biohydrolyzable phosphate analogues, but are not limited to the specific embodiments. Preferably, the prodrug of the compound having a carboxyl functional group is low alkyl ester of a carboxylic acid. The carboxylic ester is usually formed by esterifying a part of the carboxylic acid present in the molecule. The prodrug may be easily prepared using well known method, such as those described in Burger's Medicinal Chemistry and Drug Discovery 6thed. (Donald J. Abrahamed., 2001, Wiley) and Design and Application of Prodrugs (H. Bundgaard ed., 1985, Harwood Academic Publishers Gmfh).

The present invention provides a hydrogen peroxide scavenger including the aminoaromatic compound of Chemical Formula 1 and the pharmaceutically acceptable salt thereof as an effective component.

In addition, the present invention provides a pharmaceutical composition for preventing or treating neurodegenerative diseases, including the aminoaromatic compound of Chemical Formula 1 or the pharmaceutically acceptable salt thereof as an effective component.

The neurodegenerative disease is a disease or condition meaning abnormal motor control ability, cognitive impairment, perceptual disorder, sensory dysfunction, and autonomic nerve dysfunction in which the function of the nervous system of the subject is impaired, and has the same meaning as "degenerative brain disease". Specifically, it may be exemplified as dementia, Alzheimer's disease (AD), Parkinson's disease (PD), Huntington's disease, Lou Gehrig's disease (ALS), post-traumatic stress disorder (trauma), multiple sclerosis (MS), cerebral ischemia disease, amyotrophic lateral sclerosis, and the like.

The aminoaromatic compound according to the present invention decomposes overproduced hydrogen peroxide in the presence of a heme-containing peroxidase present in vivo, blood hemoglobin (Hb) to lower a blood hydrogen peroxide level to an appropriate level, resulting in inhibition or treatment of onset of neurodegenerative diseases.

In addition, the aminoaromatic compound according to the present invention is a small molecule blood hydrogen peroxide scavenger and has very high blood-brain barrier (BBB) permeability and acts directly on the brain, thereby showing an excellent effect on brain disease treatment. Therefore, the aminoaromatic compound of the present invention may be useful for preventing or treating neurodegenerative diseases.

The pharmaceutical composition according to an exemplary embodiment further includes a common non-toxic pharmaceutically acceptable carrier and/or excipient in addition to the effective component and may be formulated into a common preparation in the pharmaceutical field, that is, a preparation for oral administration or a preparation for parenteral administration. In addition, a diluent such as a filler, an extender, a binder, a wetting agent, a disintegrant, and a surfactant may be further included.

The pharmaceutically acceptable carrier, excipient, or diluent may be lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, and the like, but is not limited thereto.

The pharmaceutical composition of the present invention may be formulated into various forms, for example, oral formulations such as powders, granules, tablets, capsules, suspensions, emulsions, syrups, and aerosols, injections of sterile injection solutions, and the like by a common method according to the purpose of use, and may be orally administered or administered by various routes including intravenous, intraperitoneal, subcutaneous, rectal, and topical administrations.

In addition, the pharmaceutical composition of the present invention may further include a filler, an anticoagulant, a lubricant, a wetting agent, a flavoring, an emulsifying agent, an antiseptic agent, and the like.

An example of a formulation for oral administration may include tablets, pills, hard/soft capsules, solutions, suspensions, emulsifiers, syrups, granules, elixirs, and the like, and these formulations may use one or more of commonly used diluents or excipients such as fillers, extenders, wetting agents, disintegrants, lubricants, binders, and surfactants, in addition to the effective component. As a disintegrant, agar, starch, alginic acid or a sodium salt thereof, an anhydrous calcium monohydrogen phosphate salt, and the like may be used, as a lubricant, silica, talc, stearic acid, or a magnesium salt or calcium salt thereof, polyethylene glycol, and the like may be used, and as a binder, magnesium aluminum silicate, starch paste, gelatin, tragacanth, methyl cellulose, sodium carboxymethyl cellulose, polyvinylpyrrolidine, low-substituted hydroxypropyl cellulose, and the like may be used. Other than that, lactose, dextrose, sucrose, mannitol, sorbitol, cellulose, glycine, and the like may be used as a diluent, and if necessary, commonly known effervescent mixtures, absorbents, colorants, flavoring agents, sweetening agents, and the like may be used therewith.

An example of a preparation for parenteral administration may include sterile aqueous solutions, non-aqueous solvent, suspensions, emulsions, freeze-dried preparations, suppositories, and the like. As the non-aqueous solvent and the suspension, propylene glycol, polyethylene glycol, a vegetable oil such as an olive oil, an injectable ester such as ethyloleate, and the like may be used. As a base of the suppository, witepsol, macrogol, tween 61, cacao butter, laurin butter, glycerol, gelatin, and the like may be used. Meanwhile, an injection may include a conventional additive such as a solubilizer, an isotonic agent, a suspending agent, an emulsifying agent, a stabilizer, and an antiseptic agent. For formulation into the injection, the aminoaromatic compound of the present invention or the pharmaceutically acceptable salt thereof is mixed in water with a stabilizer or a buffer to prepare a solution or a suspension, which may be produced into a unit dosage form of an ampule or vial.

The pharmaceutical composition of the present invention may be sterilized, may further include an adjuvant such as an antiseptic agent, a stabilizer, a thickener, a hydrating agent or an emulsifying accelerator, a salt for regulating osmotic pressure, and/or a buffer, or may further include other therapeutically useful materials, and may be formulated according to a conventional method such as dissolution, dispersion, mixing, granulation, gelling, or coating.

The pharmaceutically effective amount of the aminoaromatic compound of the present invention may be determined by factors including the health state of a patient, the kind of diseases, severity, an activity of a drug, a sensitivity to a drug, an administration manner, an administration time, administration route and releasing rate, a treatment period, combination, and a simultaneously used drug, and other factors well known in the medical field. Specifically, the effective amount of the compound in the pharmaceutical composition of the present invention may vary depending on the age, the gender, and the weight of a patent, and generally, about 0.01 to 500 mg/kg/day, preferably 0.1 to 100 mg/kg/day may be administered every day or every other day or administered in a divided dose of 1 to 3 times a day. However, since the amount may be increased or decreased depending on an administration route, severity of the disease, gender, weight, age, and the like, the administration amount does not limit the scope of the present invention in any way.

The pharmaceutical composition of the present invention may be orally or parenterally administered, and parenteral administration such as subcutaneous, intravenous, intramuscular, or intraperitoneal injection is preferred.

The pharmaceutical composition of the present invention may be administered as an individual therapeutic agent or in combination with other therapeutic agents, may be administered sequentially or simultaneously with a conventional therapeutic agent, and may be administered in a single or multiple doses. Taking the factors into account, it is important to administer the composition in a minimum amount to obtain a maximum effect without any side effect, and this will be easily determined by a person skilled in the art.

In addition, the present invention provides a method of preventing or treating neurodegenerative diseases including administering the aminoaromatic compound or the pharmaceutically acceptable salt thereof, or the pharmaceutical composition to an individual having or at risk of developing neurodegenerative diseases.

In addition, the present invention provides a method of preventing or treating neurodegenerative diseases including administering the aminoaromatic compound or the pharmaceutically acceptable salt thereof, or the pharmaceutical composition to an individual having or at risk of developing neurodegenerative diseases.

In addition, the present invention is to provide a health functional food composition for preventing or ameliorating neurodegenerative diseases, including the aminoaromatic compound of the present invention or a sitologically acceptable salt thereof as an effective component.

The sitologically acceptable salt may be obtained by reacting the aminoaromatic compound of the present invention with an inorganic acid such as hydrochloric acid, hydrobromic acid, sulfuric acid, nitric acid, and phosphoric acid, a sulfonic acid such as methanesulfonic acid, ethanesulfonic acid, and p-toluenesulfonic acid, or an organic carbonic acid such as tartaric acid, formic acid, citric acid, acetic acid, trichloroacetic acid, trifluoroacetic acid, capric acid, isobutanic acid, malonic acid, succinic acid, phthalic acid, gluconic acid, benzoic acid, lactic acid, fumaric acid, maleic acid, and salicylic acid. In addition, it may be obtained by reacting the compound of the present invention with a base to form an ammonium salt, an alkali metal salt such as sodium or potassium salt, alkaline earth metal salt such as calcium or magnesium salt, a salt of organic bases such as dicyclohexylamine, N-methyl-D-glucamine, and tris(hydroxymethyl)methylamine, and an amino acid salt such as arginine and lysine, and is not limited thereto.

The health functional food composition may be provided in the form of powder, granules, tablets, capsules, a syrup, or a beverage, and the health functional food is used with other food or a food additive in addition to the aminoaromatic compound as the effective component and may be appropriately used according to a common method. The mixed amount of the effective component may be appropriately determined according to its purpose of use, for example, prevention, health or therapeutic treatment.

The health functional food composition may include various nutritional supplements, vitamins, minerals (electrolyte), flavors such as synthetic flavors and natural flavors, colorants and enhancers (cheese, chocolate, etc.), pectic acid and salts thereof, alginic acid and salts thereof, organic acids, protective colloid thickeners, pH regulators, stabilizers, preservatives, glycerin, alcohol, carbonation agent used in carbonated drink, and the like. Other than that, fruit pulp for preparing natural fruit juice, fruit juice drink, and vegetable drink may be included. These components may be used independently or in combination.

In addition, the health functional food may further include food additives, and whether it is appropriate as "food additives" is determined by the specification and the standards for the relevant item in accordance with the general rules and general test methods of the food additive code approved by the Korea Food & Drug Administration, unless otherwise stipulated.

The items listed in the "food additive code" include, for example, chemical synthetics such as ketones, glycine, potassium citrate, nicotinic acid, and cinnamic acid, natural additives such as persimmon pigment, licorice extract, crystalline cellulose, and guar gum, and mixed preparations such as sodium L-glutamate preparation, alkaline additives for noodles, preservative preparation, and tar colorant preparation.

The aminoaromatic compound included in the health functional food composition may be used according to the effective dose of the pharmaceutical composition, but in the case of long-term intake for the purpose of health and hygiene or for the purpose of health control, may be used below the range, and since the effective component has no problem in terms of safety, it may be used in the amount above the range, of course.

The health functional food composition may be formulated into various formulations such as meat, sausage, bread, chocolate, candies, snacks, confectionery, pizza, ramen, other noodles, chewing gum, dairy products including ice cream, various soups, beverages, tea, drinks, alcoholic beverages, and vitamin complexes.

Hereinafter, the present invention will be described in detail through the following preferred exemplary embodiments. However, this is presented by way of illustration of the present invention, and the right scope of the present invention is not limited thereby in any sense and the right scope of the present invention is only defined by the claims set forth below.

[Preparation Example 1] Preparation of tert-butyl (4-aminophenyl)(methyl)carbamate

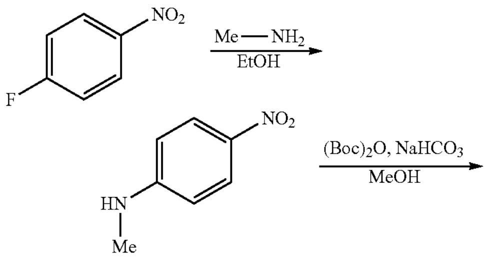

-continued

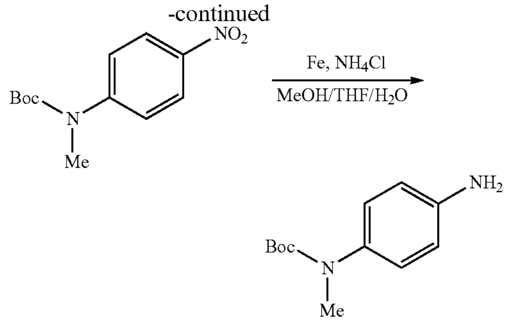

Preparation of N-Methyl-4-Nitroaniline

Fluoro-4-nitrobenzene (1.0 g, 7.1 mmol) and methylamine (3.41 g, 109.9 mmol) were dissolved in ethanol, and the solution was refluxed for 24 hours. Thereafter, the solution was cooled to room temperature, and the solvent was removed under reduced pressure. An organic layer was separated from the residue by ethyl acetate and brine and washed. The separated organic layer was dried with sodium sulfate, and ethyl acetate was removed under reduced pressure to obtain 913.3 mg (84.6%) of the title compound as a yellow solid. 400 MHz $^1$H NMR (DMSO-d$_6$) δ 8.01 (d, 2H, J=9.28), 7.31 (d, 1H, J=4.28), 6.61 (d, 2H, J=9.36), 2.80 (d, 2H, J=5.00), 2.33 (s, 1H)

Preparation of Tert-Butylmethyl (4-Nitrophenyl) Carbamate

N-methyl-4-nitroaniline (800 mg, 5.26 mmol), di-tert-butyl dicarbonate (1.72 g, 7.89 mmol), and 4-dimethylaminopyridine (32.1 mg, 0.26 mmol) were dissolved in tetrahydrofuran, and the solution was refluxed for 12 hours. Thereafter, the solution was cooled to room temperature, and the solvent was removed under reduced pressure. An organic layer was separated from the residue by ethyl acetate and brine and washed. The separated organic layer was dried with sodium sulfate, and ethyl acetate was removed under reduced pressure to obtain 1.29 g (97.3%) of the title compound as a yellow oil. 400 MHz $^1$H NMR (DMSO-d$_6$) δ 8.20 (d, 2H, J=9.20), 7.60 (d, 2H, J=9.16), 3.29 (s, 3H), 1.45 (s, 9H)

Preparation of Tert-Butyl (4-Aminophenyl)(Methyl)Carbamate tert-Butylmethyl(nitrophenyl) carbamate (1.29 g, 5.11 mmol) was dissolved in a mixed solvent of distilled water (12 mL), methanol (25 mL), and tetrahydrofuran (6 mL), iron powder (1.36 g, 26.1 mmol) and ammonium chloride (2.80 g, 52.4 mmol) were added thereto, and stirring was performed at 50° C. for 3 hours. Thereafter, the solution was cooled to room temperature and filtered with celite. After filtration, the solvent was removed under reduced pressure. An organic layer was separated from the residue by ethyl acetate and brine and washed. The separated organic layer was dried with sodium sulfate, and ethyl acetate was removed under reduced pressure to obtain 890 mg (78.1%) of the title compound as a yellow solid. 400 MHz 1H NMR (DMSO-d$_6$) δ 6.86 (d, 2H, J=8.52), 6.50 (d, 2H, J=8.60), 5.01 (s, 2H), 3.06 (s, 3H), 1.35 (s, 9H)

Example 1: Preparation of Aminoaromatic Compound

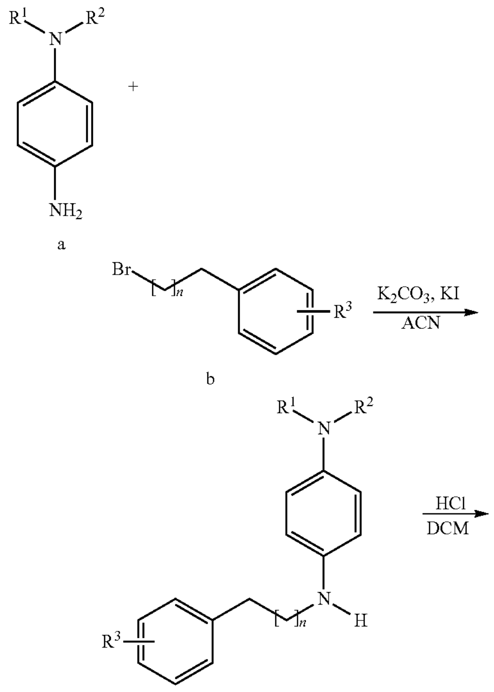

P1

-continued

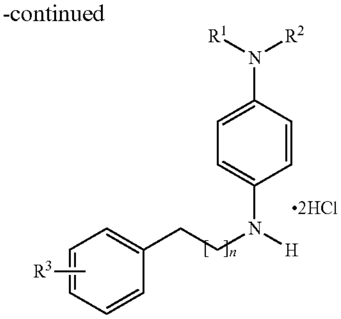

P2

To an acetonitrile solution in which a p-phenylenediamine compound (a, 1.2 equivalent) was dissolved, potassium carbonate (3.0 equivalent), potassium iodide (0.1 equivalent), and a phenylalkyl bromide compound (b, 1.0 equivalent) were added, and the mixture was stirred at 110° C. for 36 hours. Thereafter, it was cooled to room temperature, diluted with ethyl acetate, and washed with brine. The remaining organic layer was dried with $Na_2SO_4$, and then the solvent was removed under reduced. The residue was purified by a column to obtain a compound P1. The purified compound P1 was dissolved in dichloromethane (DCM), and a 4.0 M hydrogen chloride solution was added thereto. Thereafter, the solution was stirred at room temperature for 48 hours, and the produced precipitate was filtered to obtain a compound P2 in a hydrochloride form.

Various aminoaromatic compounds in the following Table 1 were prepared using the above described method:

TABLE 1

| Examples | Compound structure | Yield Description | $^1H$ NMR data |
|---|---|---|---|
| 1 | 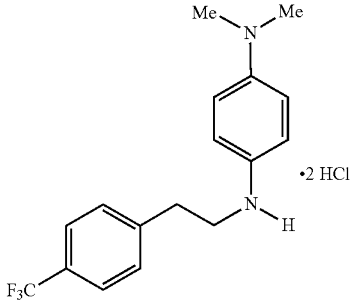 KSD12008 | 86.4% White solid | 400 MHz $^1H$ NMR (DMSO-$d_6$) δ 7.66 (d, 2H, J = 8.00), 7.51 (d, 2H, J = 7.96), 7.40 (s, 2H), 6.89 (s, 2H), 3.36 (t, 2H, J = 7.28), 3.01 (s, 6H), 2.98 (t, 3H, J = 7.04) |
| 2 | 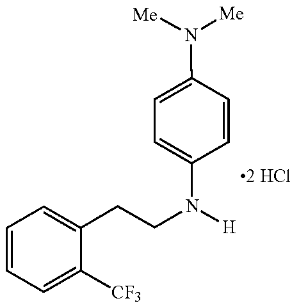 KSD12010 | 60.1% White solid | 400 MHz $^1H$ NMR (MeOD-$d_4$) δ 7.71 (d, 1H, J = 8.00), 7.60 (t, 2H, J = 7.52), 7.51 (d, 1H, J = 7.72), 7.46 (d, 2H, J = 9.08), 7.05 (d, 2H, J = 9.04), 3.50 (t, 2H, J = 7.56), 3.25 (s, 6H), 3.16 (t, 2H, J = 8.32) |

TABLE 1-continued
| Examples | Compound structure | Yield Description | $^1$H NMR data |
| --- | --- | --- | --- |
| 3 | 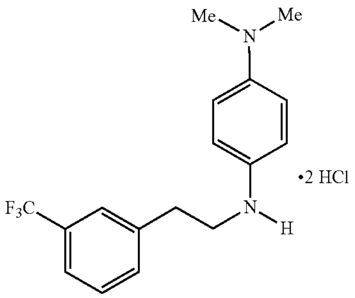 KSD12011 | 99.7% White solid | 400 MHz $^1$H NMR (MeOD-$d_4$) δ 7.56 (d, 2H, J = 15.52), 7.53 (d, 2H, J = 7.76), 7.49 (d, 2H, J = 9.04), 7.16 (d, 2H, J = 9.00), 3.57 (t, 2H, J = 7.28), 3.31 (s, 6H), 3.07 (t, 2H, J = 7.36) |
| 4 | 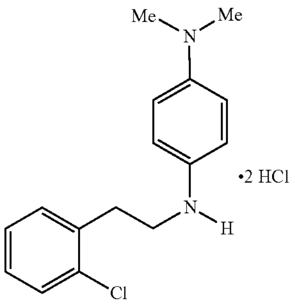 KSD12012 | 54.4% White solid | 400 MHz $^1$H NMR (MeOD-$d_4$) δ 7.50 (d, 2H, J = 9.04), 7.40 (m, 1H), 7.35 (m, 1H), 7.25 (m, 2H), 7.18 (d, 2H, J = 9.04), 3.52 (t, 2H, J = 7.60), 3.24 (s, 6H), 3.12 (t, 2H, J = 8.04) |
| 5 | 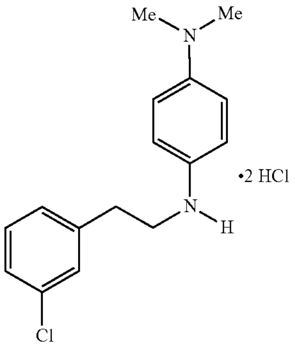 KSD12013 | 54.4% White solid | 400 MHz $^1$H NMR (MeOD-$d_4$) δ 7.54 (d, 2H, J = 9.20), 7.31 (d, 2H, J = 7.60), 7.27 (d, 2H, J = 11.20), 7.21 (d, 2H, J = 7.60), 3.55 (t, 2H, J = 7.2), 3.24 (s, 6H), 3.00 (t, 2H, J = 7.6) |
| 6 | 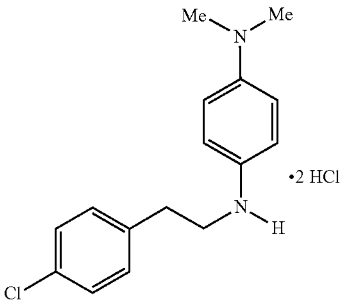 KSD12014 | 54.4% White solid | 400 MHz $^1$H NMR (MeOD-$d_4$) δ 7.34 (d, 2H, J = 9.00) 7.30 (d, 2H, J = 10.28), 7.24 (d, 2H, J = 8.36), 6.99, 2H, J = 9.00), 3.46 (t, 2H, J = 7.28), 3.31 (s, 6H), 2.93 (t, 2H, J = 7.64) |

TABLE 1-continued

| Examples | Compound structure | Yield Description | $^1$H NMR data |
|---|---|---|---|
| 7 | 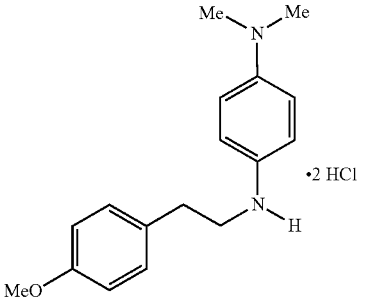 KSD12015 | 25.0% White solid | 400 MHz $^1$H NMR (MeOD-$d_4$) δ 7.29 (d, 2H, J = 9.04), 7.16 (d, 2H, J = 8.64), 7.04 (d, 2H, J = 9.00), 6.86 (d, 2H, J = 8.68), 3.77 (s, 3H), 3.43 (t, 2H, J = 7.4), 3.17 (s, 6H) |
| 8 | 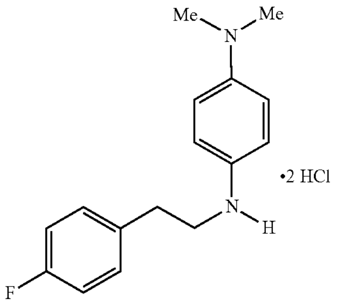 KSD12016 | 72.0% White solid | 400 MHz $^1$H NMR (MeOD-$d_4$) δ 7.64 (d, 2H, J = 9.00), 7.40 (d, 2H, 9.00), 7.30 (m, 2H), 7.05 (t, 2H, J = 8.72), 3.57 (t, 2H, J = 7.60), 3.26 (s, 6H), 3.02 (t, 2H, J = 8.04) |
| 9 | 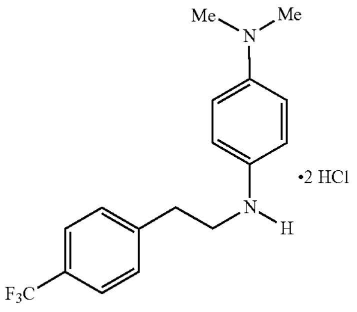 KSD12018 | 86.4% Brown solid | 400 MHz $^1$H NMR (MeOD-$d_4$) δ 7.64 (d, 2H, J = 8.08), 7.50 (d, 2H, J = 8.08), 7.47 (s, 4H), 3.65 (t, 2H, J = 7.60), 3.15 (t, 2H, J = 8.16), 2.88 (t, 2H, J = 7.36), |
| 10 | 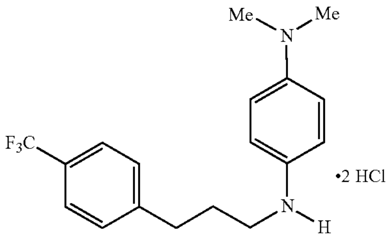 KSD12019 | 46.7% Pink solid | 400 MHz $^1$H NMR (MeOD-$d_4$) δ 7.59 (d, 2H, J = 8.12), 7.52 (d, 2H, J = 8.96), 7.42 (d, 2H, J = 8.04), 7.30 (d, 2H, J = 8.92), 3.34 (t, 2H, J = 7.60), 3.23 (s, 6H), 2.85 (t, 2H, J = 7.68), 2.05 (quint, 2H, J = 7.48) |
| 11 | 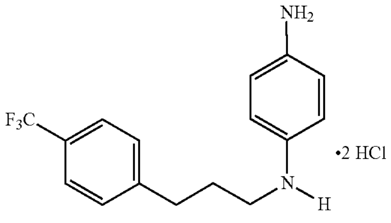 KSD12021 | 77.2% Brown solid | 400 MHz $^1$H NMR (MeOD-$d_4$) δ 7.60 (d, 4H, J = 8.48), 7.55 (d, 2H, J = 8.76), 7.43 (d, 2H, J = 7.96), 3.43 (t, 2H, J = 7.76), 2.86 (t, 2H, J = 7.68), 2.10 (quint, 2H, J = 7.60) |

TABLE 1-continued
| Examples | Compound structure | Yield Description | $^1$H NMR data |
|---|---|---|---|
| 12 | 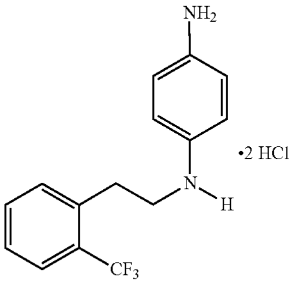 KSD12026 | 93.1% Violet solid | 400 MHz $^1$H NMR (MeOD-$d_4$) δ 7.70 (d, 1H, J = 7.88), 7.60 (t, 1H, J = 7.40), 7.52, (d, 1H, J = 7.64), 7.44 (t, 1H, J = 7.60), 7.39 (d, 2H, J = 8.8), 7.26 (d, 2H, J = 8.8), 3.54 (t, 2H, J = 7.84), 3.18 (t, 2H, J = 8.56) |
| 13 | 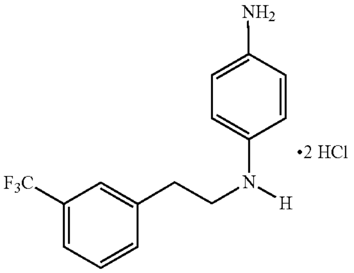 KSD12027 | 82.7% Brown solid | 400 MHz $^1$H NMR (MeOD-$d_4$) δ 7.61 (s, 1H), 7.56 (m, 2H), 7.54 (d, 1H, J = 7.68), 7.24), 7.45 (m, 4H), 3.64 (t, 2H, J = 3.14 (t, 2H, J = 3.14) |
| 14 | 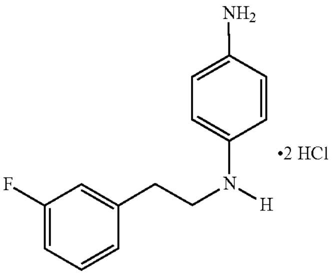 KSD12028 | 91.2% Brown solid | 400 MHz $^1$H NMR (MeOD-$d_4$) δ 7.48 (s, 4H) 7.34 (q, 1H, J = 6.28), 7.11 (d, 1H, J = 7.88), 7.06 (d, 1H, J = 9.92), 6.98 (t, 1H, J = 8.64), 3.63 (t, 2H, J = 8.04), 3.07 (t, 2H, J = 8.08) |
| 15 | 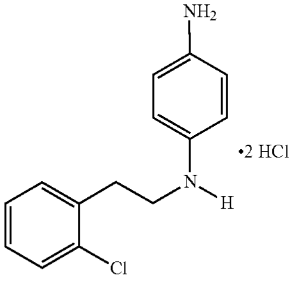 KSD12029 | 77.9% White solid | 400 MHz $^1$H NMR (MeOD-$d_4$) δ 7.42 (m, 1H), 7.40 (m, 2H), 7.35 (m, 2H), 7.33 (m, 1H), 7.27 (m, 2H), 3.56 (t, 2H, J = 7.76), 3.16 (t, 2H, J = 8.16) |

TABLE 1-continued

| Examples | Compound structure | Yield Description | $^{1}$H NMR data |
|---|---|---|---|
| 16 | 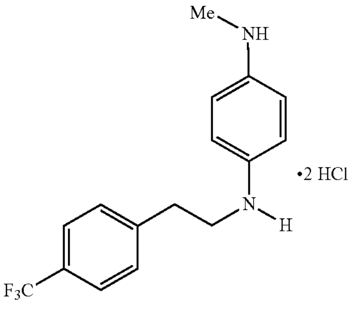 KSD12017 | 91.8% White solid | 400 MHz $^{1}$H NMR (MeOD-$d_4$) δ 7.62 (d, 2H, J = 8.12), 7.48 (d, 2H, J = 8.08), 7.41 (d, 2H, J = 8.88), 7.28 (d, 2H, J = 8.84), 3.60 (t, 2H, J = 7.44), 3.10 (d, 2H, J = 7.84), 3.03 (s, 3H) |
| 17 | 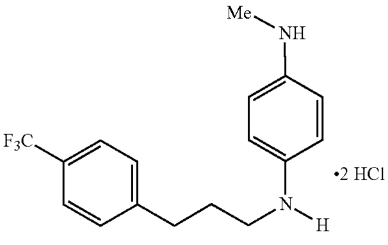 KSD12020 | 77.9% Violet solid | 400 MHz $^{1}$H NMR (MeOD-$d_4$) δ 7.60 (d, 2H, J = 8.16), 7.42 (d, 2H, J = 8.12), 7.39 (d, 2H, J = 8.96), 7.34 (d, 2H, J = 8.92), 3.36 (t, 2H, J = 7.64), 3.02 (s, 3H), 2.84 (t, 2H, J = 7.72), 2.06 (quint, 2H, J = 7.60) |
| 18 | 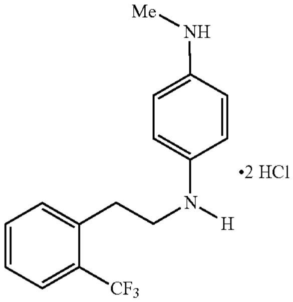 KSD12022 | 72.3% White solid | 400 MHz $^{1}$H NMR (MeOD-$d_4$) δ 7.69 (d, 1H, J = 7.88), 7.59 (t, 1H, J = 7.32), 7.50 (d, 1H, J = 7.60), 7.43 (t, 1H, J = 7.56), 7.33 (d, 2H, J = 8.92), 712 (d, 2H, J = 8.92), 3.50 (t, 2H, J = 7.72), 3.15 (t, 2H, J = 8.56), 3.01 (s, 3H) |
| 19 | 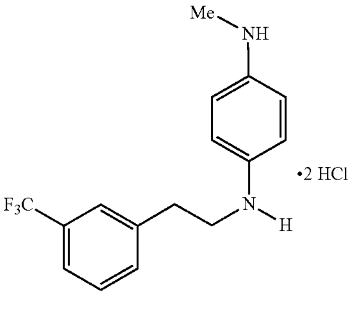 KSD12023 | 95.6% White solid | 400 MHz $^{1}$H NMR (MeOD-$d_4$) δ 7.55 (m, 4H), 7.43 (d, 2H, J = 8.92), 7.30 (d, 2H, J = 8.88), 3.60 (t, 2H, J = 7.88), 3.11 (t, 2H, J = 8.00), 3.03 (s, 3H) |

TABLE 1-continued
| Examples | Compound structure | Yield Description | $^1H$ NMR data |
|---|---|---|---|
| 20 | 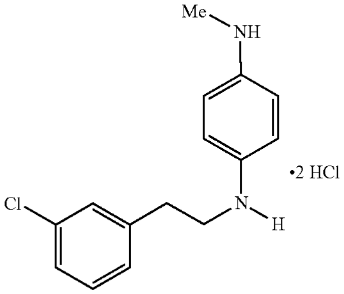 KSD12024 | 95.4% White solid | 400 MHz $^1H$ NMR (MeOD-$d_4$) δ 7.29 (t, 4H, J = 7.24), 7.22 (m, 2H), 7.14 (d, 2H, J = 8.88), 3.53 (t, 2H, J = 7.36), 3.00 (s, 3H), 2.99 (t, 2H, J = 7.88) |
| 21 | 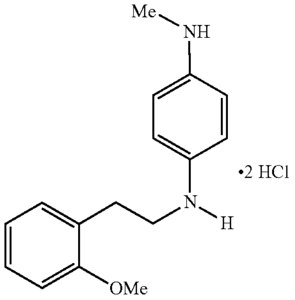 KSD12025 | 91.2% White solid | 400 MHz $^1H$ NMR (MeOD-$d_4$) δ 7.34 (s, 4H), 7.25 (m, 1H), 7.17 (m, 1H), 6.97 (d, 2H, J = 7.88), 6.90 (m, 1H), 3.85 (s, 3H), 3.52 (t, 2H, J = 7.68), 3.01 (s, 3H), 3.01 (t, 2H, J = 7.88) |
| 22 | 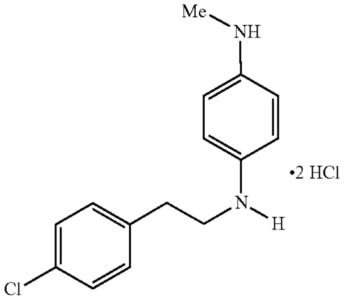 KSD12032 | 80.5% White solid | 400 MHz $^1H$ NMR (MeOD-$d_4$) δ 7.31 (d, 2H, J = 8.52), 7.22 (m, 4H), 7.03 (d, 2H, J = 8.92), 3.47 (t, 2H, J = 7.32), 2.98 (s, 3H), 2.94 (t, 2H, J = 7.76) |
| 23 | 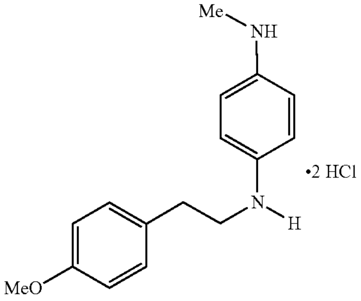 KSD12033 | 65.0% White solid | 400 MHz $^1H$ NMR (MeOD-$d_4$) δ 7.43 (m, 4H), 7.19 (d, 2H, J = 8.64), 6.88 (d, 2H, J = 8.64), 3.77 (s, 3H), 3.55 (t, 2H, J = 7.72), 3.04 (s, 3H), 2.96 (t, 2H, J = 8.08) |

TABLE 1-continued

| Examples | Compound structure | Yield Description | $^1H$ NMR data |
|---|---|---|---|
| 24 | 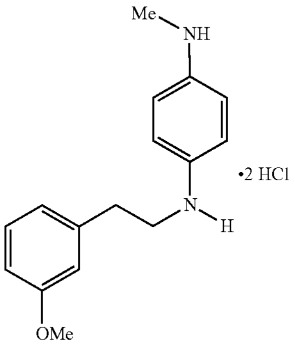 KSD12034 | 87.3% White solid | 400 MHz $^1H$ NMR (MeOD-$d_4$) δ 7.45 (d, 2H, J = 11.56), 7.39 (d, 2H, J = 9.00), 7.26 (t, 1H, J = 8.08), 6.86 (m, 3H), 3.81 (s, 3H), 3.61 (t, 2H, J = 7.68), 3.06 (s, 3H), 3.02 (t, 2H, J = 8.04) |

Experimental Examples

Primary Cultured Astrocyte

Primary cortical astrocytes were prepared from C57BL/6 mice from the day of birth to day 3 since birth. The cerebral cortex was dissected without adherent meninges, minced, and dissociated into a single cell suspension by trituration. The cells were grown in Dulbecco's modified Eagle's medium (DMEM) (Invitrogen) supplemented with 25 mM glucose, 10% heat-inactivated horse serum, 10% heat-inactivated fetal calf serum (FCS), 2 mM glutamine, and 1,000 U/ml of penicillin-streptomycin. Culture was maintained at 37° C. in a humidified 5% $CO_2$ incubator. On day 3 of the culture, cells were vigorously washed by repeated pipetting, and the medium was exchanged to remove debris and other floating cell types.

[Experimental Example 1] Assessment of Hydrogen Peroxide Scavenging Ability by Enzyme Present In Vivo In order to investigate hydrogen peroxide scavenging ability by the suggested enzyme and the aminoaromatic compound of the present invention, the following experiment was performed.

Figure 1:
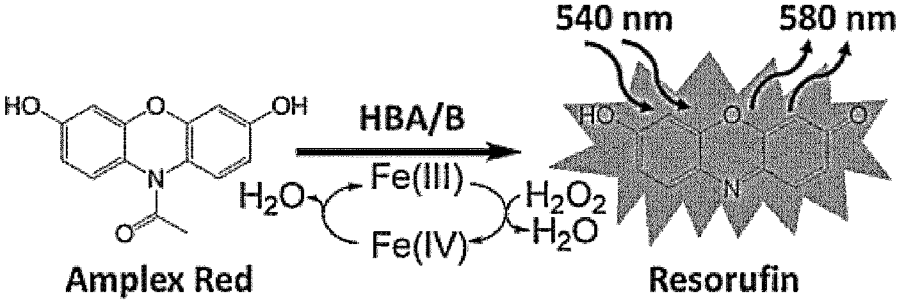
FIG. 1—a schematic image of hydrogen peroxide ($H_2O_2$) analysis by a hemoglobin enzymatic reaction between hydrogen peroxide ($H_2O_2$) and 10-acetyl-3,7-dihydroxyphenoxazine (Amplex Red).

Amplex Red is a means which turns into a fluorescent substance called resorufin when horse radish peroxidase (HRP) and $H_2O_2$ exist together and allows measurement of changes in $H_2O_2$, that is, $H_2O_2$ assay. However, HRP is an enzyme which does not exist in the body, and the experiment was performed based on the idea that hemoglobin is a group having the same heme as HRP and may act with the aminoaromatic compound of the present invention. The experiment was performed by adding hemoglobin instead of HRP to the $H_2O_2$ assay by Amplex Red (FIG. 1). The final concentration of each substance was 10 μM of $H_2O_2$ and 80 μg/ml of hemoglobin, and the aminoaromatic compound of the present invention was treated by concentration. After the reaction at 37° C. for about 30 minutes as such, fluorescence (excitation: 540 nm, emission: 580 nm) was measured by a microplate reader. At this time, it can be said that fluorescence is proportional to the amount of $H_2O_2$. Normalization was performed for each concentration based on a fluorescence value without a drug, and a value at which the fluorescence value was 50%, that is, a half maximal effective concentration ($EC_{50}$) was determined by a program through statistical processing. The results are shown in the following Table 2, and AAD-2004 was used as a control group.

TABLE 2

| Examples | Compound structure | Hb-$EC_{50}$ (μM) |
|---|---|---|
| 1 | 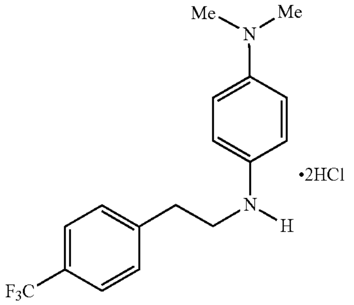 KSD12008 | 0.54 |
| 3 | 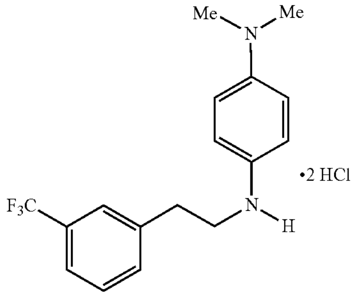 KSD12011 | 0.56 |

TABLE 2-continued
| Examples | Compound structure | Hb-$EC_{50}$ (μM) |
| --- | --- | --- |
| 4 | 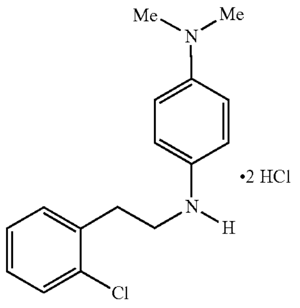 KSD12012 | 0.58 |
| 5 | 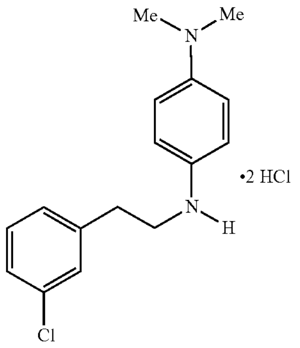 KSD12013 | 0.43 |
| 6 | 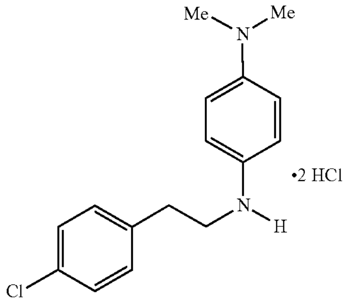 KSD12014 | 0.27 |
| 7 | 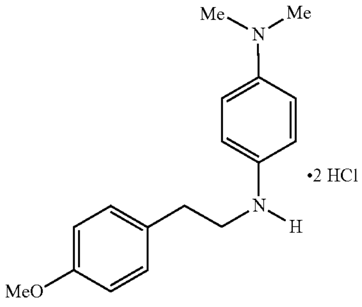 KSD12015 | 0.46 |
| 8 | 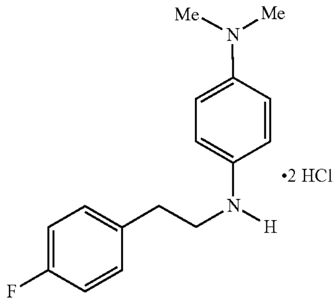 KSD12016 | 0.41 |
| 9 | 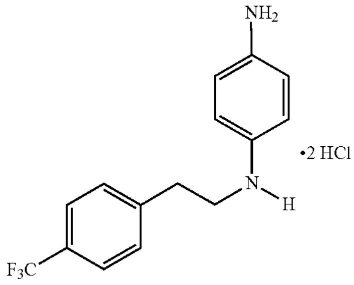 KSD12018 | 0.30 |
| 10 | 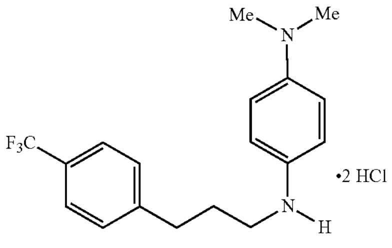 KSD12019 | 0.3 (DMSO) |
| 11 | 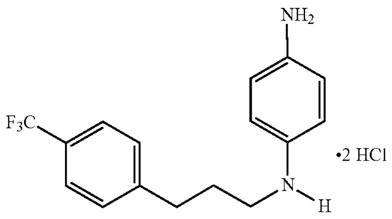 KSD12021 | 0.54 (DMSO) |
| 12 | 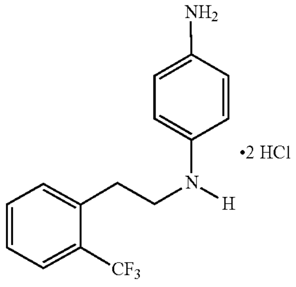 KSD12026 | 0.83 |

TABLE 2-continued
| Examples | Compound structure | Hb-EC$_{50}$ (μM) |
|---|---|---|
| 13 | 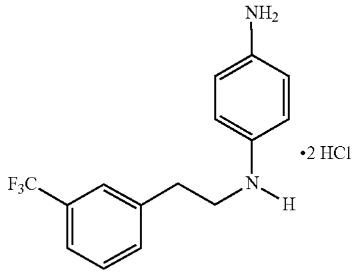 KSD12027 | 0.72 |
| 14 | 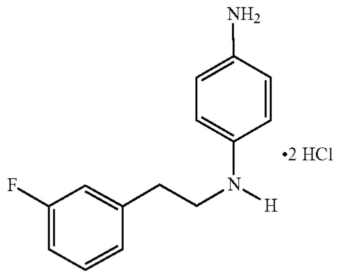 KSD12028 | 0.78 |
| 15 | 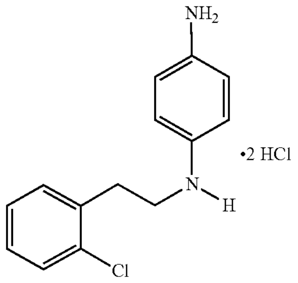 KSD12029 | 0.59 |
| 16 | 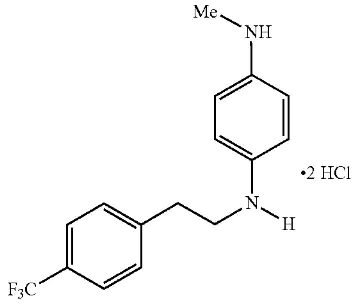 KSD12017 | 0.19 |
| 17 | 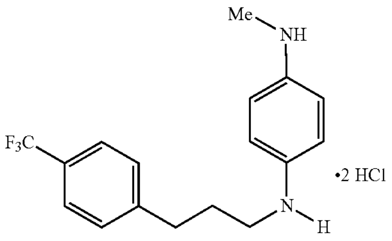 KSD12020 | 0.3 (DMSO) |
TABLE 2-continued
| Examples | Compound structure | Hb-EC$_{50}$ (μM) |
|---|---|---|
| 18 | 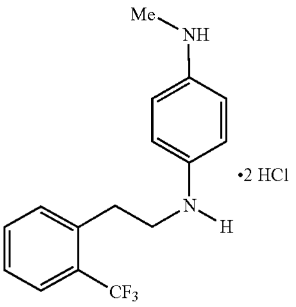 KSD12022 | 0.21 |
| 19 | 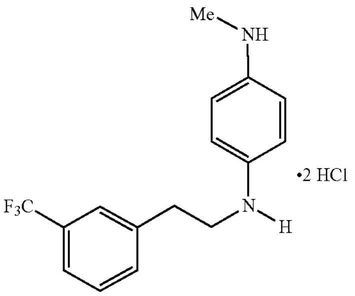 KSD12023 | 0.19 |
| 20 | 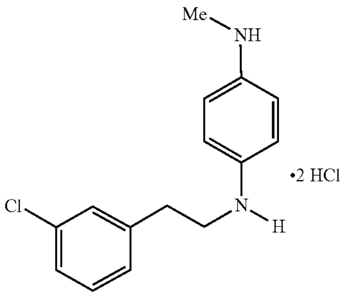 KSD12024 | 0.26 |
| 21 | 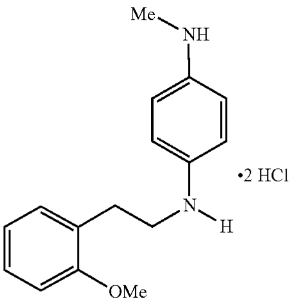 KSD12025 | 0.06 |

TABLE 2-continued

| Examples | Compound structure | Hb-$EC_{50}$ (μM) |
|---|---|---|
| 22 | 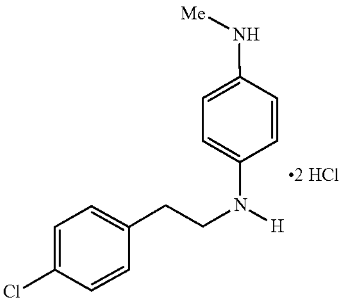 KSD12032 | 0.52 |
| 23 | 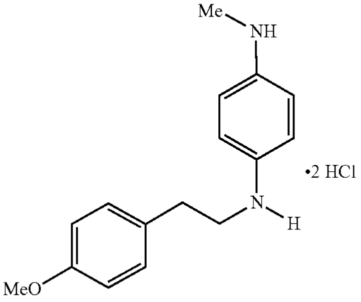 KSD12033 | 0.62 |
| 24 | 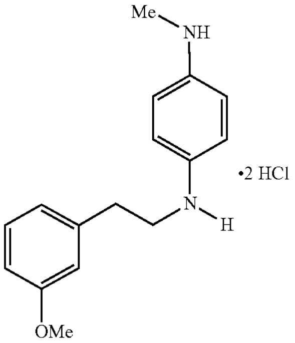 KSD12034 | 0.61 |
| Control group | 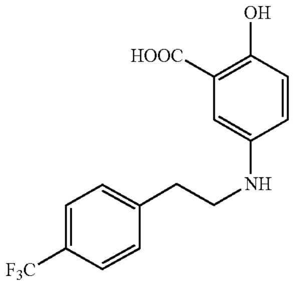 AAD-2004 | 0.99 |

As shown in Table 2, the aminoaromatic compound according to the present invention effectively reacted with hemoglobin (Hb) to decrease hydrogen peroxide. Therefore, it is shown that the aminoaromatic compound according to the present invention is useful as a hydrogen peroxide scavenger which acts with hemoglobin present in the body to decrease overproduced hydrogen peroxide to an appropriate level.

Figure 2:
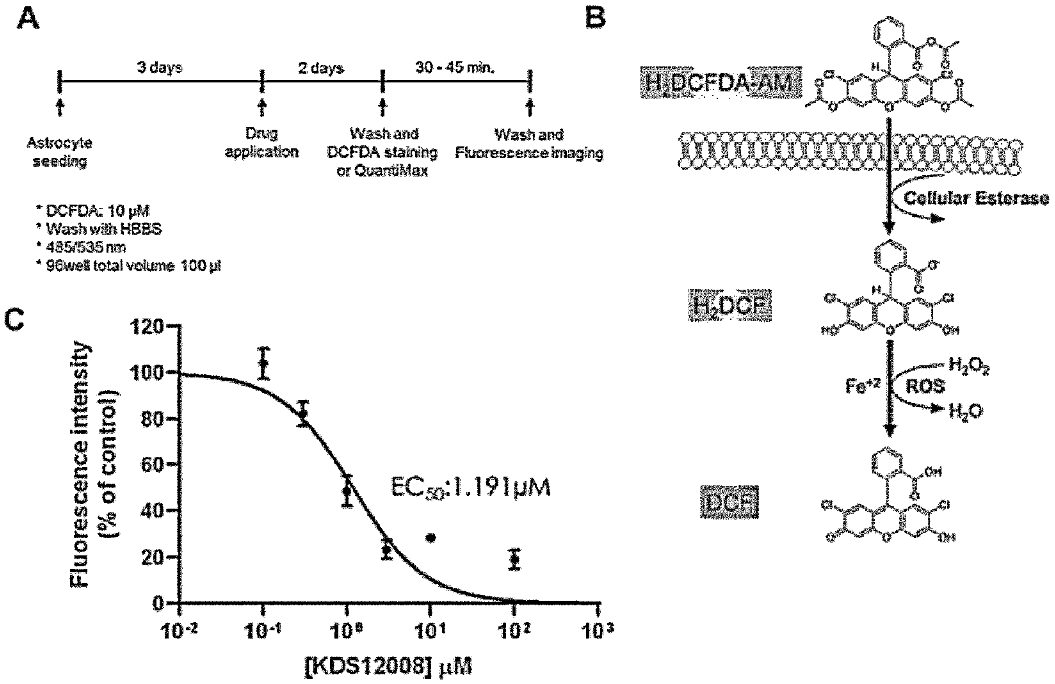
FIG. 2—analysis I of in vitro $H_2O_2$ decomposition of a novel compound of Experimental Example 2 [(A, B) chemical reaction schematic diagram showing a timeline of imaging using cell-permeable $H_2O_2$ dye, $H_2$DCFDA-AM and the measurement principle of hydrogen peroxide in primary cultured astrocytes; (C) a graph showing fluorescence intensity depending on a concentration of the aminoaromatic compound of the present invention, KDS12008 (Example 1). The fluorescence intensity represents an amount of $H_2O_2$ in cells, which was normalized by control conditions.].

[Experimental Example 2] $H_2O_2$ Decomposition Experiment I In Vitro and Cell Viability Assessment In order to verify that there was a $H_2O_2$ scavenging effect in a cell-level experiment, a cell-permeant 2',7'-dichlorodihydrofluorescein diacetate ($H_2$DCFDA-AM) drug which is a hydrogen peroxide probe in astrocytes was used to measure the amount of $H_2O_2$ in the cells with fluorescence (A and B of FIG. 2). The aminoaromatic compound of the present invention, KDS12008 (Example 1) was used as a test substance, and sodium pyruvate which is known to remove $H_2O_2$ was used as a control material. It was confirmed that when the astrocytes were treated with the aminoaromatic compound of the present invention, KDS12008 (Example 1) at various concentrations, $H_2O_2$ was decreased with the concentration (C of FIG. 2).

Figure 3:
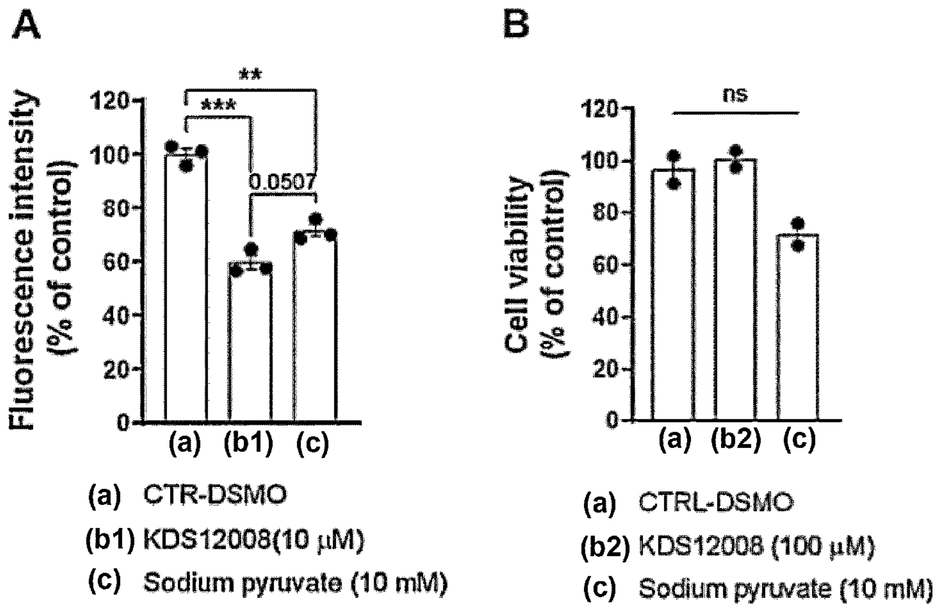
FIG. 3—the results of analysis I of in vitro $H_2O_2$ decomposition of the novel compound of Experimental Example 2

An experiment timeline for investigating the $H_2O_2$ decomposition effect by the aminoaromatic compound of the present invention, KDS12008 (Example 1) (10 μM) and sodium pyruvate (10 mM) for naturally occurring $H_2O_2$ in the cultured astrocytes is shown in A of FIG. 2. 3 days passed so that the cultured astrocytes were at rest, and the aminoaromatic compound of the present invention, KDS12008 (Example 1) and sodium pyruvate were treated. After 2 days, a cell permeable $H_2O_2$ dye ($H_2$DCFDA-AM) was used as a method of measuring intracellular $H_2O_2$. $H_2$DCFDA-AM was a sample which reacted with $H_2O_2$ to produce green fluorescence, and was used at 10 μM for measurement. The results are shown in A of FIG. 3. From A of FIG. 3, when the aminoaromatic compound of the present invention, KDS12008 (Example 1) (10 μM) was used, a statistically significant decrease in $H_2O_2$ was confirmed, and a decreasing $H_2O_2$ trend as compared with 10 mM sodium pyruvate at a high concentration was shown.

In addition, in order to investigate cell viability, the experiment was performed using a QuantiMax reagent. The cell viability was confirmed by a luminescence degree of QuantiMax, and the results are shown in B of FIG. 3. From B of FIG. 3, it is shown that while sodium pyruvate lowered cell viability, the aminoaromatic compound of the present invention, KDS12008 (Example 1) had no effect on cell viability despite a concentration of 100 μM higher than a concentration used when measuring $H_2O_2$ decomposition effect of 10 μM. That is, it showed significantly better efficiency than conventionally known substances.

[Experimental Example 3] Passive Avoidance Test (PAT) I

A passive avoidance test is an experiment to check the memory of animals, in which a weak electric stimulation was given in a dark room and it was assessed whether the animal remembered the electrical stimulation.

Since mice preferred a dark room, they have a tendency to move quickly to a dark room when they are in a bright room. However, when mice are given a weak electrical stimulation in a dark room, they remembered a dark room and an electrical stimulation in combination, and thus, they do not move from a bright room to a dark room. A time to move from a bright room to a dark room (latency to dark room, sec) was measured, thereby measuring memory of a combination of the electrical stimulation and the dark room.

An APP/PS1 mouse which is used as an Alzheimer's animal model was used to perform the passive avoidance test (FIG. 4). A wild type (WT) mouse was used as a control group.

On the first day of PAT, as an acquisition session, the mouse was allowed to stay in a bright room, and after a certain time, a dark room was opened and a time for the mouse to enter the dark room was measured. When the mouse entered the dark room, an electrical shock (0.5 mA, 2 sec) was given by a foothold. On the second day, as a retrieval session, the mouse was placed in a bright room, and a time for the mouse to enter a dark room was measured. At this time, the door of the dark room was opened first. When the mouse has a good memory, it does not enter the dark room with the memory of the electrical stimulation, and when the mouse has a bad memory, it quickly enters the dark room again. Since the WT mouse has a memory of receiving an electrical stimulation on the previous day (acquisition session), it does not try to enter the dark room. However, since the APP/PS1 dementia mouse does not remember that it had an electrical stimulation in the dark room, it easily enters the dark room.

The APP/PS1 dementia mouse was intraperitoneally injected with the aminoaromatic compound of the present invention (KDS12008 (Example 1), KDS12017 (Example 16), or KDS12025 (Example 21)) (KDS12008 (Example 1) 30 mg/kg/day (30 mpk); KDS12017 (Example 16) 30 mg/kg/day (30 mpk); KDS12025 (Example 21) 3 mg/kg/day (3 mpk)) for 16 days (intraperitoneal injection, IP). On the 26th day, the passive avoidance test was performed, and it was confirmed that the impaired memory of the APP/PS1 dementia mouse was significantly recovered (FIG. 4).

That is, the Alzheimer's model APP/PS1 mouse had a worse memory than the wild type mouse, but it was confirmed that the APP/PS1 mouse to which the aminoaromatic compound of the present invention (KDS12008 (Example 1), KDS12017 (Example 16), or KDS12025 (Example 21)) was administered had an improved memory of passive avoidance and showed a tendency of a significantly increased stay time. Therefore, the aminoaromatic compound of the present invention had an effect on Alzheimer's disease.

[Experimental Example 4] Histochemical Staining of Brain Tissue (Immunohistochemistry, IHC) I The brain of the Alzheimer's animal model of Experimental Example 3 was fixed with formaldehyde, and sliced into a small thickness. The amount of cells or specific protein in the sliced brain was measured with an image by histochemical staining. In the present experimental example, an antibody labeling an astrocyte was used to measure a change in astrocytes related to dementia. The results are illustrated in FIG. 5. That is, in the present experimental example, the hippocampus of the brain was histologically stained and a change in astrocytes around dementia substance amyloid beta was observed. Glial fibrillary acidic protein (GFAP) refers to astrocytes staining, 4',6-diamidino-2-phenylindole (DAPI) marked cell nuclei and amyloid beta substance.

Changes, such as amyloid beta accumulation in the hippocampus of the Alzheimer's animal model and the astrocytes becoming reactive astrocytes in pathological conditions such as Alzheimer's disease were confirmed by the previous research. At this time, the astrocytes produced an inhibitory neurotransmitter, GABA, and hydrogen peroxide to inhibit nerves and induce brain cell (neuron) death to worsen dementia. However, the tendency to decrease in astrocytes by an anti-dementia drug was also confirmed by the previous research.

It was confirmed from FIG. 5 that the Alzheimer's animal model showed the symptoms of astrocytes by increased GFAP, but the mouse treated with the aminoaromatic compound of the present invention, KDS12008 (Example 1), KDS12017 (Example 16), or KDS21025 (Example 21), respectively had decreased GFAP. Thus, it was confirmed that the astrocyte which is the cause of Alzheimer's disease was effectively decreased, which is the effect expressed by removal hydrogen peroxide.

[Experimental Example 5] Passive Avoidance Test (PAT) II 3 mg/kg/day (3 mpk) and 10 mg/kg/day (10 mpk) of the aminoaromatic compound of the present invention, KDS12025 (Example 21) was intraperitoneally injected into the APP/PS1 mouse which is used as an Alzheimer's animal model for one week, and the passive avoidance test was performed in the same manner as in Experimental Example 3. The results are illustrated in FIG. 6.

A healthy normal mouse (wild type, WT) remembered the electrical stimulation in the retrieval process well, so that the time for the mouse to enter the dark room where it was given the electrical stimulation was long, but a control group which was an Alzheimer's animal model but was not treated with a drug (WT+saline) forgot the electrical stimulation and entered the dark room where it was given the electrical stimulation soon.

However, the Alzheimer's model APP/PS1 mouse treated with the aminoaromatic compound of the present invention, KDS12025 (Example 21) at 3 mg/kg/day (3 mpk) and 10 mg/kg/day (10 mpk) maintained its memory similarly to the healthy normal mouse despite a decreased drug administration from previous 16 days to one week, and thus, showed a statistically significant difference from the Alzheimer's model APP/PS1 mouse (FIG. 6). Therefore, the aminoaromatic compound of the present invention had an effect on Alzheimer's disease.

[Experimental Example 6] Histochemical Staining of Brain Tissue (Immunohistochemistry, IHC) II The Alzheimer's animal model of Experimental Example 5 was used to perform histochemical staining of the brain tissue in the same manner as in Experimental Example 4, and the results are shown in FIG. 7. FIG. 7 showed immunohistochemistry (IHC) staining of the hippocampus tissue of the animal model, in which GFAP refers to the results of astrocytes staining, and Aβ refers to the results of amyloid beta staining.

From FIG. 7, it was confirmed that the astrocytes were increased in the Alzheimer's animal model, but the astrocytes returned to a healthy normal level in the APP/PS1 mouse treated with 3 mg/kg/day or 10 mg/kg/day of the aminoaromatic compound of the present invention, KDS21025 (Example 21). This result is consistent with the behavioral test results of Experimental Example 5, and it was shown that overproduced $H_2O_2$ returned to a normal level by the treatment with the aminoaromatic compound of the present invention.

[Experimental Example 7] Electrophysiology Experiment

The Alzheimer's animal model of Experimental Example 5 was used to confirm the influence of astrocytes and the mechanism causing memory impairment in dementia through an electrophysiology experiment.

In the previous research, a mechanism causing memory and cognitive impairments in an Alzheimer's group by continuous secretion of an inhibitory neurotransmitter called tonic GABA or tonic current by reactive astrocytes has been proved, and the change may be confirmed by electrophysiology.

Therefore, in the present experimental example, each of the APP/PS1 mouse as the Alzheimer's animal model, the APP/PS1 mouse treated with 3 mg/kg/day or 10 mg/kg/day, respectively, of the aminoaromatic compound of the present invention, KDS12025 (Example 21), and a healthy normal mouse (wild type, WT) was anesthetized, and brain tissues were obtained therefrom to measure an electrical signal of living hippocampus cells. Thus, the tonic GABA which inhibits neurotransmission in a brain cell was measured. The results are illustrated in FIG. 8.

The Alzheimer's animal model (APP/PS1, TG) had increased tonic GABA as compared with the healthy normal mouse (WT), but the Alzheimer's animal model treated with the aminoaromatic compound of the present invention, KDS12025 (Example 21) had decreased tonic GABA. In the present experiment, a change in tonic GABA was electrophysiologically confirmed, and the efficacy of the aminoaromatic compound of the present invention, that is, the inhibition ability of the tonic GABA to inhibit neurotransmission, was verified therefrom. Therefore, the aminoaromatic compound of the present invention had an effect on Alzheimer's disease.

[Experimental Example 8] Novel Place Recognition Experiment and Passive Avoidance Test (PAT)

The cognitive function related to hippocampus was assessed by a novel place recognition experiment to confirm the cognitive impairment and recovery. The same objects were put for a certain period of time for interaction, and after one hour, the position of only one object was changed. When having a normal cognitive function, a past memory is maintained to grow interest in a new object, but when having cognitive impairment, a new place is not determined. At this time, as an animal model, an APP/PS1+GiD Alzheimer's mode mouse which is a more closely developed model mouse to the phenomenon shown in the Alzheimer's dementia patient was used. The APP/PS1+GiD Alzheimer's model mouse was produced referring to Nature Neuroscience 23, 1555-1566 (2020).

In the present experiment, APP/PS1+GiD was produced by injecting AAV-GFAP104-DTR-GFP virus into the hippocampus of the APP/PS1 mouse, and hereinafter, is referred to as "APP+DTR". In addition, the product obtained by injecting AAV-GFAP104-GFP virus into the hippocampus of the APP/PS1 mouse was referred to as "APP+GFP". In addition, APP+DTR to which the aminoaromatic compound of the present invention, KDS12025 (Example 21) was administered was referred to as "APP+DTR+KDS12025". In addition, as the WT mouse, APP/PS1 and littermate were used, and the product obtained by injecting AAV-GFAP104-GFP virus into the hippocampus of the WT mouse was referred to as "WT+GFP" and the product obtained by injecting AAV-GFAP104-DTR-GFP virus into the hippocampus of the WT mouse was referred to as "WT+DTR".

A normal mouse (WT+GFP, WT+DTR) had a normal cognitive function. APP+GFP showed a similar level of cognitive function to the normal mouse, but APP+DTR showed an impaired cognitive function like an Alzheimer's patient. When the APP/PS1+GiD Alzheimer's model mouse which showed impaired cognitive function, that is, APP+DTR, was intraperitoneally injected with 3 mg/kg/day of the aminoaromatic compound of the present invention, KDS12025 (Example 21) (i.p.) (that is, APP+DTR+KDS12025), a recovered cognitive function was confirmed (FIG. 9).

In addition, as a result of PAT, the normal mouse (WT+GFP) remembered the dark room where it was given an electrical stimulation well and took a long time to enter the dark room. However, the APP/PS1+GiD Alzheimer's model mouse, that is, APP+DTR showed a problem in memory, but when the aminoaromatic compound of the present invention, KDS12025 (Example 21) was administered, that is, in the case of APP+DTR+KDS12025, recovered memory was shown (FIG. 10).

That is, the hydrogen peroxide removal efficacy of the aminoaromatic compound of the present invention was confirmed in the APP/PS1+GiD Alzheimer's mode mouse which is a more closely developed model mouse to the phenomenon shown in the Alzheimer's dementia patient, and thus, the effect on the Alzheimer's disease was shown.

[Experimental Example 9] Single Toxicity Assessment (Lethal Dose 50, LD50)

The aminoaromatic compound of the present invention, KDS12008 (Example 1), KDS12017 (Example 16), or KDS12025 (Example 21) was intraperitoneally injected at a single dose of 100, 300, and 1000 mg/kg, respectively, into a WT mouse at about 8 weeks of age (C57BL/6 mouse), and it was assessed whether the animal was dead. The results are shown in FIGS. 11 to 13. As a result, all of three drugs showed toxicity at a concentration of 1000 mg/kg. However, it was confirmed that only about 50% of the animals died at 300 mg/kg of the three drugs, and a lethal toxicity was not shown in the mouse at a lower concentration of 100 mg/kg of the all of three drugs.

[Experimental Example 10] Blood Brain Barrier (BBB) Permeability Analysis

Based on J Med Chem. 2001 Mar. 15; 44 (6):923-30., an artificial blood brain barrier (BBB) was produced by a parallel artificial membrane permeability assay (PAMPA), and the permeability of the drug was assessed.

As a result, it was confirmed that the aminoaromatic compound of the present invention, KDS12025 (Example 21) permeated BBB at a concentration of 50 μM with a high permeability (KDS12025 (Example 21) $67.43\times10^{-6}$ cm/sec). However, it was confirmed that a conventional drug AAD-2004 which is expected to remove reactive oxygen had a significantly low BBB permeability of $3.56\times10^{-6}$ cm/sec at the same concentration. Therefore, it was confirmed that the aminoaromatic compound of the present invention had high permeability.

Hereinabove, although the present invention has been described by specific matters, limited exemplary embodiments, and drawings, they have been provided only for assisting the entire understanding of the present invention, and the present invention is not limited to the exemplary embodiments, and various modifications and changes may be made by those skilled in the art to which the present invention pertains from the description.

Therefore, the spirit of the present invention should not be limited to the above-described exemplary embodiments, and the following claims as well as all modifications equal or equivalent to the claims are intended to fall within the scope and spirit of the invention.

The invention claimed is:

1. An aminoaromatic compound represented by the following Chemical Formula 1 or a pharmaceutically acceptable salt thereof:

[Chemical Formula 1]

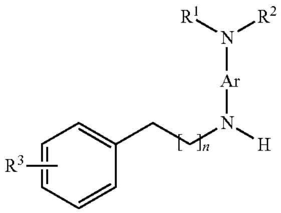

wherein

Ar is $C_6$-$C_{20}$ arylene, and the arylene of Ar may be further substituted by one or more selected from $C_1$-$C_{10}$ alkyl, $C_1$-$C_{10}$ alkoxy, amino, mono- or di-$C_1$-$C_{10}$ alkylamino, halo$C_1$-$C_{10}$ alkyl, and halo$C_1$-$C_{10}$ alkoxy and hydroxy;

$R^1$ is hydrogen or $C_1$-$C_{10}$ alkyl;

$R^2$ is $C_1$-$C_{10}$ alkyl;

$R^3$ is halogen, $C_1$-$C_{10}$ alkoxy, halo$C_1$-$C_{10}$ alkyl, or halo$C_1$-$C_{10}$ alkoxy; and n is an integer of 1 or 2;

provided that $R^3$ is halogen, n is an integer of 1.

2. The aminoaromatic compound or the pharmaceutically acceptable salt thereof of claim 1, wherein Ar is phenylene or biphenylene; and may be further substituted with one or more selected from $C_1$-$C_7$ alkyl, $C_1$-$C_7$ alkoxy, amino, and hydroxy.

3. The aminoaromatic compound or the pharmaceutically acceptable salt thereof of claim 1, wherein the aminoaromatic compound is represented by the following Chemical Formula 2:

[Chemical Formula 2]

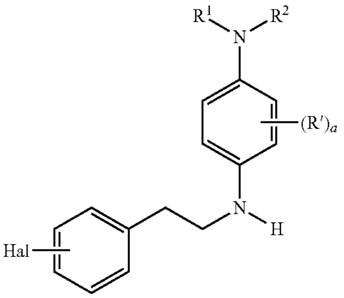

wherein $R^1$ is hydrogen or $C_1$-$C_7$ alkyl;

$R^2$ is $C_1$-$C_7$ alkyl;

Hal is halogen;

R' is $C_1$-$C_7$ alkyl, $C_1$-$C_7$ alkoxy, amino, or hydroxy; and a is an integer of 0 to 4.

4. The aminoaromatic compound or the pharmaceutically acceptable salt thereof of claim 1, wherein the aminoaromatic compound is represented by the following Chemical Formula 3:

[Chemical Formula 3]

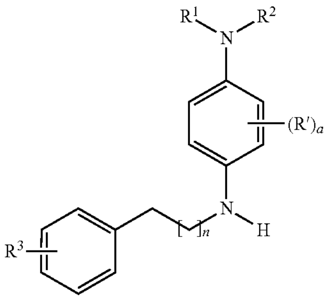

wherein $R^1$ is hydrogen or $C_1$-$C_7$ alkyl;

$R^2$ is $C_1$-$C_7$ alkyl;

$R^3$ is $C_1$-$C_7$ alkoxy or halo$C_1$-$C_7$ alkyl;

R' is $C_1$-$C_7$ alkyl, $C_1$-$C_7$ alkoxy, amino, or hydroxy;

a is an integer of 0 to 4; and n is an integer of 1 or 2.

5. The aminoaromatic compound or the pharmaceutically acceptable salt thereof of claim 3, wherein $R^1$ is hydrogen or $C_1$-$C_4$ alkyl; $R^2$ is $C_1$-$C_4$ alkyl; Hal is halogen; and a is an integer of 0.

6. The aminoaromatic compound or the pharmaceutically acceptable salt thereof of claim 4, wherein $R^1$ is hydrogen or $C_1$-$C_4$ alkyl; $R^2$ is $C_1$-$C_4$ alkyl; $R^3$ is $C_1$-$C_4$ alkoxy or halo$C_1$-$C_4$ alkyl; a is an integer of 0; and n is an integer of 1 or 2.

7. The aminoaromatic compound or the pharmaceutically acceptable salt thereof of claim 3, wherein the aminoaromatic compound is any one selected from the following compound group:

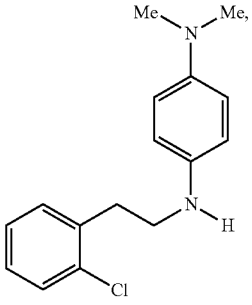

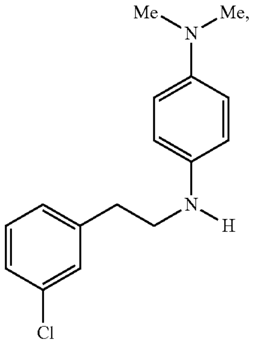

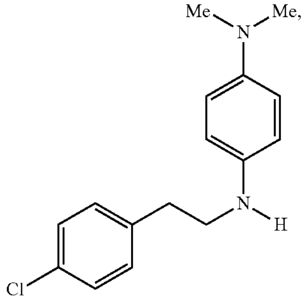

-continued
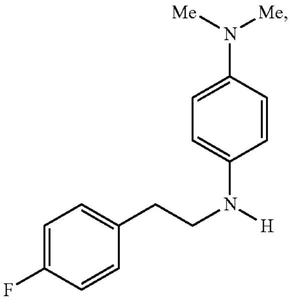
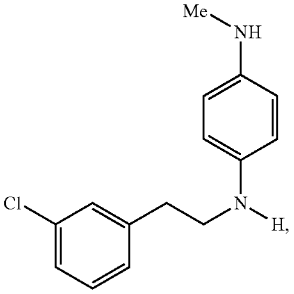
and
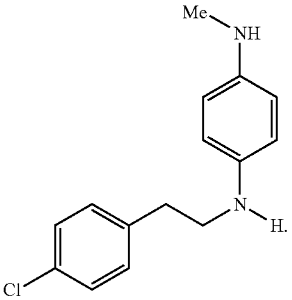
8. The aminoaromatic compound or the pharmaceutically acceptable salt thereof of claim 4, wherein the aminoaromatic compound is any one selected from the following compound group:
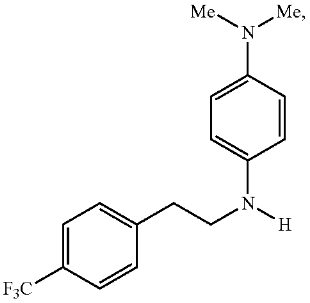
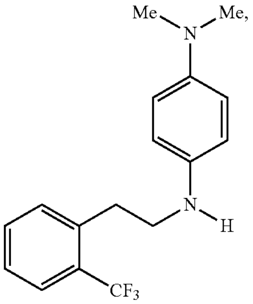
-continued
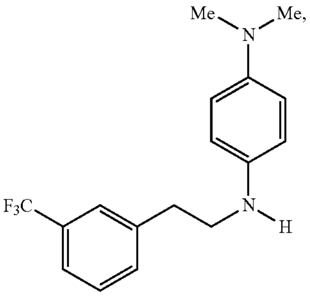
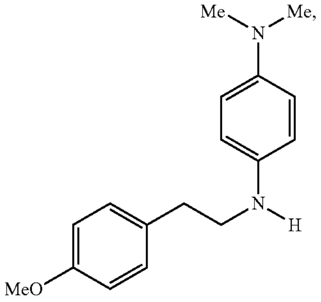
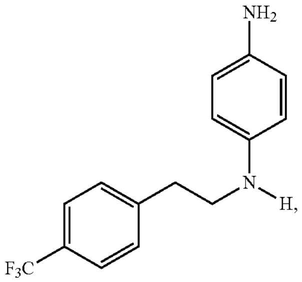
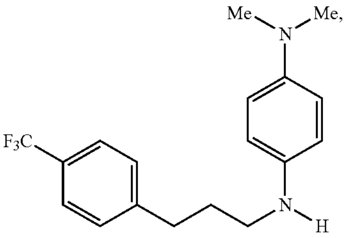
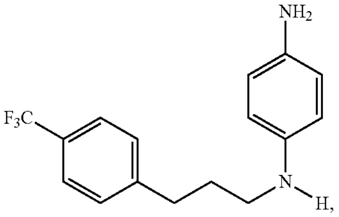
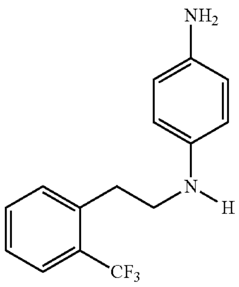

-continued

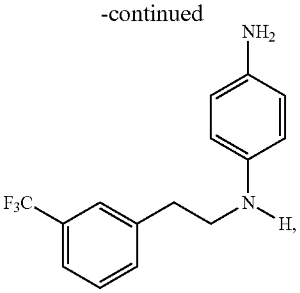

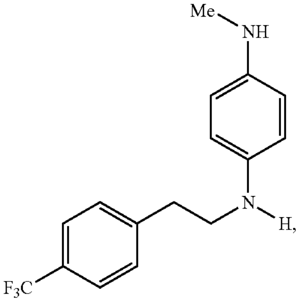

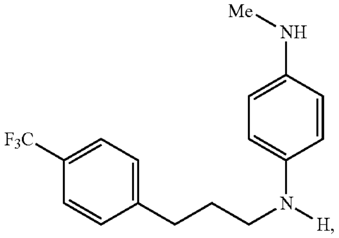

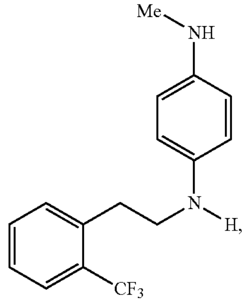

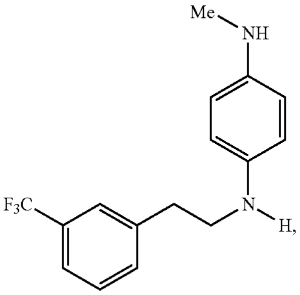

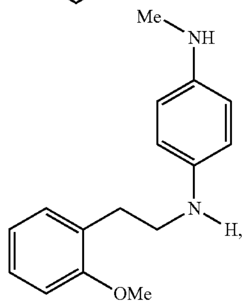

-continued

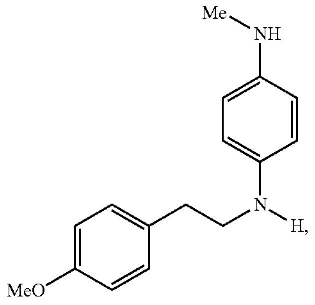

and

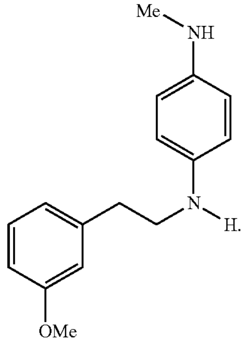

9. The aminoaromatic compound or the pharmaceutically acceptable salt thereof of claim 1, wherein the pharmaceutically acceptable salt is a hydrochloride.

10. A pharmaceutical composition for treating or preventing neurodegenerative diseases comprising the aminoaromatic compound or the pharmaceutically acceptable salt of claim 1 as an effective component.

11. The pharmaceutical composition of claim 10, further comprising an excipient and a carrier.

12. The pharmaceutical composition of claim 10, wherein the neurodegenerative disease is dementia, Alzheimer's disease (AD), Parkinson's disease (PD), Huntington's disease, Lou Gehrig's disease (ALS), post-traumatic stress disorder (trauma), multiple sclerosis (MS), cerebral ischemia disease, or amyotrophic lateral sclerosis.

13. A method of preventing or treating neurodegenerative diseases comprising administrating the pharmaceutical composition of claim 10 to an individual which has or is at risk of the neurodegenerative disease.

14. A health functional food composition for preventing or ameliorating neurodegenerative diseases comprising the aminoaromatic compound of claim 1 or a sitologically acceptable salt thereof as an effective component.

* * * * *